(12) United States Patent
Neoh

(10) Patent No.: US 10,195,398 B2
(45) Date of Patent: Feb. 5, 2019

(54) TENSION MEMBER SEAL AND SECURING MECHANISM FOR MEDICAL DEVICES

(71) Applicant: WenHong Neoh, Bloomington, IN (US)

(72) Inventor: WenHong Neoh, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 626 days.

(21) Appl. No.: 14/812,512

(22) Filed: Jul. 29, 2015

(65) Prior Publication Data

US 2016/0045712 A1    Feb. 18, 2016

Related U.S. Application Data

(60) Provisional application No. 62/036,764, filed on Aug. 13, 2014.

(51) Int. Cl.
*A61M 25/01* (2006.01)
*A61B 17/29* (2006.01)
*A61B 17/00* (2006.01)

(52) U.S. Cl.
CPC ............ *A61M 25/0147* (2013.01); *A61B 2017/00323* (2013.01); *A61B 2017/00473* (2013.01); *A61B 2017/2948* (2013.01); *A61M 2025/015* (2013.01)

(58) Field of Classification Search
CPC ........ A61M 25/0147; A61M 2025/015; A61M 5/3015; A61M 25/0152; A61M 2025/0161; A61M 2025/0163; A61M 13/00; A61M 5/2015; A61M 35/006; A61B 2017/2948; A61B 2017/00473; A61B 2017/00323
See application file for complete search history.

(56) References Cited

U.S. PATENT DOCUMENTS

| | | |
|---|---|---|
| 2,649,092 A | 8/1953 | Wallace |
| 3,521,620 A | 7/1970 | Cook |
| 3,625,200 A | 12/1971 | Muller |
| 4,726,374 A | 2/1988 | Bales et al. |
| 4,790,812 A | 12/1988 | Hawkins et al. |
| 4,826,087 A | 5/1989 | Chinery |

(Continued)

FOREIGN PATENT DOCUMENTS

| | | |
|---|---|---|
| CA | 2403030 | 3/2003 |
| EP | 2368481 | 9/2011 |

(Continued)

OTHER PUBLICATIONS

Non-final Office Action dated Sep. 15, 2009 U.S. Appl. No. 11/800,292.

(Continued)

*Primary Examiner* — Lauren P Farrar
(74) *Attorney, Agent, or Firm* — Buchanan Van Tuinen LLC

(57) ABSTRACT

Tension member seals and securing mechanisms for medical devices are described herein. An example embodiment of a tension member seal comprises an elongate member, a first plug, a second plug, a material disposed within a chamber defined by the elongate member, and a tension member. The elongate member has a first configuration and a second configuration and the material is configured to seal the chamber as the elongate member is moved between its first and second configurations.

15 Claims, 9 Drawing Sheets

(56) References Cited

U.S. PATENT DOCUMENTS

| | | |
|---|---|---|
| 4,886,067 A | 12/1989 | Palermo |
| 5,125,395 A | 6/1992 | Adair |
| 5,308,318 A | 5/1994 | Plassche, Jr. |
| 5,380,305 A | 1/1995 | Ghouri |
| 5,441,483 A | 8/1995 | Avitall |
| 5,447,503 A | 9/1995 | Miller |
| 5,460,616 A | 10/1995 | Weinstein et al. |
| 5,477,860 A | 12/1995 | Essen-Moller |
| 5,489,278 A | 2/1996 | Abrahamson |
| 5,509,900 A | 4/1996 | Kirkman |
| 5,522,400 A | 6/1996 | Williams |
| 5,534,007 A | 7/1996 | Germain et al. |
| 5,642,736 A | 7/1997 | Avitall |
| 5,643,171 A | 7/1997 | Bradshaw et al. |
| 5,658,301 A | 8/1997 | Lamaitre et al. |
| 5,674,197 A | 10/1997 | van Muiden et al. |
| 5,685,858 A | 11/1997 | Kawand |
| 5,718,684 A | 2/1998 | Gupta |
| 5,738,664 A | 4/1998 | Erskine et al. |
| 5,769,821 A | 6/1998 | Abrahamson et al. |
| 5,807,398 A | 9/1998 | Shaknovich |
| 5,865,800 A | 2/1999 | Mirarchi et al. |
| 5,908,403 A | 6/1999 | Bosma et al. |
| 5,916,214 A | 6/1999 | Cosio et al. |
| 5,938,582 A | 8/1999 | Ciamacco et al. |
| 5,954,050 A | 9/1999 | Christopher |
| 5,989,241 A | 11/1999 | Plishka et al. |
| 6,033,378 A * | 3/2000 | Lundquist ......... A61M 25/0136 604/528 |
| 6,071,263 A | 6/2000 | Kirkman |
| 6,117,386 A | 9/2000 | Stiger |
| 6,126,649 A | 10/2000 | VanTassel et al. |
| 6,159,158 A | 12/2000 | Lowe |
| 6,159,177 A | 12/2000 | Amos, Jr. et al. |
| 6,338,735 B1 | 1/2002 | Stevens |
| 6,383,206 B1 | 5/2002 | Gillick et al. |
| 6,447,530 B1 | 9/2002 | Ostrovsky et al. |
| 6,450,988 B1 | 9/2002 | Bradshaw |
| 6,485,500 B1 | 11/2002 | Kokish et al. |
| 6,491,662 B1 | 12/2002 | Liprie et al. |
| 6,500,167 B1 | 12/2002 | Webster, Jr. |
| 6,500,182 B2 | 12/2002 | Foster |
| 6,508,833 B2 | 1/2003 | Pavcnik et al. |
| 6,527,737 B2 | 3/2003 | Kaneshige |
| 6,530,913 B1 | 3/2003 | Giba et al. |
| 6,533,783 B1 | 3/2003 | Tollner |
| 6,558,349 B1 | 5/2003 | Kirkman |
| 6,572,610 B2 | 6/2003 | Kovalcheck et al. |
| 6,629,987 B1 | 10/2003 | Gambale |
| 6,673,060 B1 | 1/2004 | Fleming, III |
| 6,679,860 B2 | 1/2004 | Stiger |
| 6,692,484 B1 | 2/2004 | Karpiel et al. |
| 6,695,858 B1 | 2/2004 | Dubrul et al. |
| 6,755,812 B2 | 6/2004 | Peterson et al. |
| 6,918,929 B2 | 7/2005 | Udipi et al. |
| 6,932,829 B2 | 8/2005 | Majercak |
| 7,037,290 B2 | 5/2006 | Gardeski et al. |
| 7,144,408 B2 | 12/2006 | Keegan et al. |
| 7,232,462 B2 | 6/2007 | Schaeffer |
| 7,269,453 B2 | 9/2007 | Mogul |
| 7,503,914 B2 | 3/2009 | Coleman et al. |
| 7,520,876 B2 | 4/2009 | Ressemann et al. |
| 7,641,630 B2 | 1/2010 | Accisano, III et al. |
| 7,658,305 B2 | 2/2010 | Voegele et al. |
| 7,678,099 B2 | 3/2010 | Ressemann et al. |
| 7,736,331 B2 | 6/2010 | Accisano, III et al. |
| 7,740,608 B2 | 6/2010 | Lampropoulos et al. |
| 7,785,252 B2 | 8/2010 | Danitz et al. |
| 7,785,315 B1 | 8/2010 | Muni et al. |
| 7,803,130 B2 | 9/2010 | Ryan et al. |
| 7,811,277 B2 | 10/2010 | Boulais |
| 7,867,218 B1 | 1/2011 | Voda |
| 7,892,233 B2 | 2/2011 | Hall et al. |
| 7,909,814 B2 | 3/2011 | Accisano, III et al. |
| 7,909,862 B2 | 3/2011 | Garrison |
| 7,935,108 B2 | 5/2011 | Baxter et al. |
| 7,959,601 B2 | 6/2011 | McDaniel et al. |
| 7,959,644 B2 | 6/2011 | Shriver |
| 8,029,461 B2 | 10/2011 | Thielen et al. |
| 8,066,664 B2 | 11/2011 | LaDuca et al. |
| 8,070,693 B2 | 12/2011 | Ayala et al. |
| 8,083,879 B2 | 12/2011 | Swinehart et al. |
| 8,118,803 B1 | 2/2012 | Chow |
| 8,182,467 B2 | 5/2012 | Nguyen et al. |
| 8,216,210 B2 | 7/2012 | Ostrovsky et al. |
| 8,369,923 B2 | 2/2013 | de la Rama et al. |
| 8,403,977 B2 | 3/2013 | Case |
| 8,425,466 B2 | 4/2013 | Sargent, Jr. |
| 8,430,864 B2 | 4/2013 | Schultz |
| 8,496,645 B2 | 7/2013 | Eells et al. |
| 8,535,310 B2 | 9/2013 | Hardin, Jr. et al. |
| 8,535,349 B2 | 9/2013 | Chen et al. |
| 8,603,185 B2 | 12/2013 | Shah et al. |
| 8,657,805 B2 | 2/2014 | Peh et al. |
| 8,734,426 B2 | 5/2014 | Ahmed et al. |
| 8,740,843 B2 | 6/2014 | Eaton et al. |
| 8,758,231 B2 | 6/2014 | Bunch et al. |
| 2001/0039450 A1 | 11/2001 | Pavcnik et al. |
| 2002/0115983 A1 | 8/2002 | Sekino et al. |
| 2003/0004460 A1 | 1/2003 | Bedell |
| 2003/0032977 A1 | 2/2003 | Brady |
| 2003/0050694 A1 | 3/2003 | Heneveld et al. |
| 2004/0087965 A1 | 5/2004 | Hebert et al. |
| 2004/0087996 A1 | 5/2004 | Forcucci et al. |
| 2004/0225322 A1 | 11/2004 | Garrison et al. |
| 2005/0171592 A1 | 8/2005 | Majercak |
| 2005/0256452 A1 | 11/2005 | DeMarchi et al. |
| 2006/0063973 A1 | 3/2006 | Makower et al. |
| 2007/0093781 A1 | 4/2007 | Kugler et al. |
| 2007/0167682 A1 | 7/2007 | Goldfarb et al. |
| 2007/0219464 A1 | 9/2007 | Davis et al. |
| 2007/0250105 A1 | 10/2007 | Ressemann et al. |
| 2007/0293727 A1 | 12/2007 | Goldfarb et al. |
| 2008/0097154 A1 | 4/2008 | Makower et al. |
| 2008/0125756 A1 | 5/2008 | Dicarlo et al. |
| 2008/0243067 A1 | 10/2008 | Rottenberg et al. |
| 2008/0249483 A1 | 10/2008 | Slenker et al. |
| 2008/0281156 A1 | 11/2008 | Makower et al. |
| 2008/0287918 A1 | 11/2008 | Rosenman et al. |
| 2009/0030274 A1 | 1/2009 | Goldfarb et al. |
| 2009/0043299 A1 | 2/2009 | Racz |
| 2009/0093823 A1 | 4/2009 | Chang et al. |
| 2009/0198153 A1 | 8/2009 | Shriver |
| 2009/0326450 A1 | 12/2009 | Ostrovsky et al. |
| 2010/0010309 A1 | 1/2010 | Kitagawa |
| 2010/0030113 A1 | 2/2010 | Morriss et al. |
| 2010/0076269 A1 | 3/2010 | Makower et al. |
| 2010/0099946 A1 | 4/2010 | Jenkins et al. |
| 2010/0211007 A1 | 8/2010 | Lesch, Jr. et al. |
| 2010/0217261 A1 | 8/2010 | Watson |
| 2010/0262075 A1 | 10/2010 | Danitz et al. |
| 2010/0280316 A1 | 11/2010 | Dietz et al. |
| 2010/0331776 A1 | 12/2010 | Salahieh et al. |
| 2011/0009700 A1 | 1/2011 | Ostrovsky et al. |
| 2011/0040269 A1 | 2/2011 | Cline |
| 2011/0112476 A1 | 5/2011 | Kauphusman et al. |
| 2011/0190831 A1 | 8/2011 | Mafi et al. |
| 2011/0218492 A1 | 9/2011 | McDaniel et al. |
| 2011/0264134 A1 | 10/2011 | Drontle et al. |
| 2011/0313392 A1 | 12/2011 | Varghese et al. |
| 2012/0046664 A1 | 2/2012 | McGuckin, Jr. et al. |
| 2012/0101441 A1 | 4/2012 | Sargent, Jr. |
| 2012/0162401 A1 | 6/2012 | Melder et al. |
| 2012/0197240 A1 | 8/2012 | Smith et al. |
| 2012/0238952 A1 | 9/2012 | Mitchell et al. |
| 2012/0265055 A1 | 10/2012 | Melsheimer et al. |
| 2012/0289940 A1* | 11/2012 | Devellian ......... A61M 25/0075 604/533 |
| 2013/0041314 A1 | 2/2013 | Dillon |
| 2013/0046138 A1 | 2/2013 | McLawhorn |
| 2013/0103004 A1 | 4/2013 | Gray et al. |
| 2013/0226146 A1 | 8/2013 | Tekulve |

(56) References Cited

U.S. PATENT DOCUMENTS

| | | |
|---|---|---|
| 2013/0238003 A1 | 9/2013 | Fischer et al. |
| 2014/0088355 A1 | 3/2014 | Schaeffer |
| 2014/0243615 A1 | 8/2014 | Schaeffer et al. |

FOREIGN PATENT DOCUMENTS

| | | |
|---|---|---|
| EP | 2710949 | 3/2014 |
| GB | 2465621 | 6/2010 |
| WO | WO98043530 | 10/1998 |
| WO | WO2001026726 | 4/2001 |
| WO | WO200170308 | 9/2001 |
| WO | WO2003001986 | 1/2003 |
| WO | WO2014134257 | 9/2014 |

OTHER PUBLICATIONS

EyeMAX CCD Laparscopes [online brochure]. Richard Wolf GmbH [retrieved Nov. 15, 2013]. Retrieved from the internet: URL: http://www.richard-wolf.com/uploads/media/A_658_Eyemax_GB_107.pdf. pp. 1-8.

EyeMAX Flexible LED Cystoscope [online brochure]. Richard Wolf GmbH [retrieved Nov. 15, 2013]. Retrieved from the internet: URL: http://www.richardwolfusa.com/fileadmin/images/content/USA_data/PDF_documents/Urology/Flexible_LED_Digital_Cystoscope_brochure_01312013.pdf. pp. 1-4.

Olympus Naso-laryngoscopes. Olympus. Retrieved from the internet: URL: www.olympuskeymed.com, pp. 1-3.

XprESS Multi-Sinus Dilation Tool Using Bending Tool. Instructions for Use, Entellus Medical, Sep. 2011, pp. 1-7.

XprESS Multi-Sinus Dilation Tool. Instructions for Use, Entellus Medical, May 2011, pp. 1-7.

A trial study of RhinoSleep for the diagnosis of sleep apnea. Psychiatry and Clinical Neurosciences. Jun. 2001, pp. 1-2.

E.G. Scan—Trans-nasal, disposable system for upper GI screening [online brochure]. SynMed Ltd. [retrieved Jun. 4, 2014]. Retrieved from the internet: URL: http://www.synmed.co.uk/products/eg_scan/pdf/SynMed_E.G.Scan_Brochure.pdf.

Drug-induced Sleep Endoscopy webpage [online], Eric J. Kezirian [retrieved Nov. 14, 2013]. Retrieved from the internet: URL: http://www.sleep-doctor.com/surgical-treatment-overview/drug-induced-sleep-endoscopy/.

EyeMax webpage [online], Richard Wolf [retrieved Nov. 14, 2013]. Retrieved from the internet: URL: http://www.richard-wolf.com/en/human-medicine/visualisation/video-endoscopes/ccd-endoscopes.html.

European Patent Office, Extended European Search Report, for International Application No. 13185810.2, dated Jan. 7, 2014, pp. 1-5.

International Searching Authority. International Search Report and Written Opinion, for International App. No. PCT/US2014/018878. dated Jun. 11, 2014. p. 1-12.

\* cited by examiner

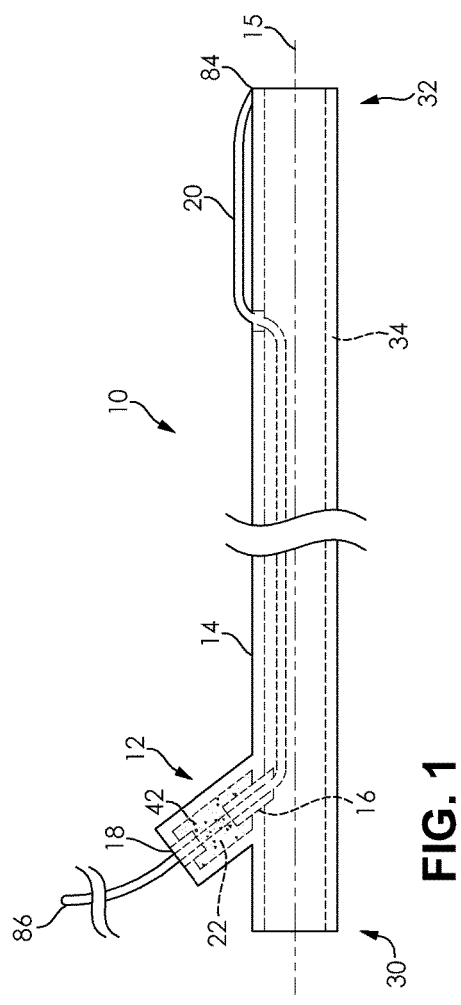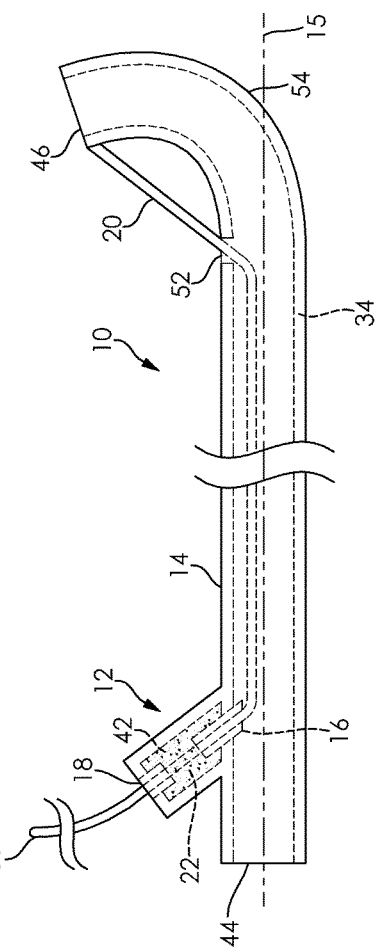

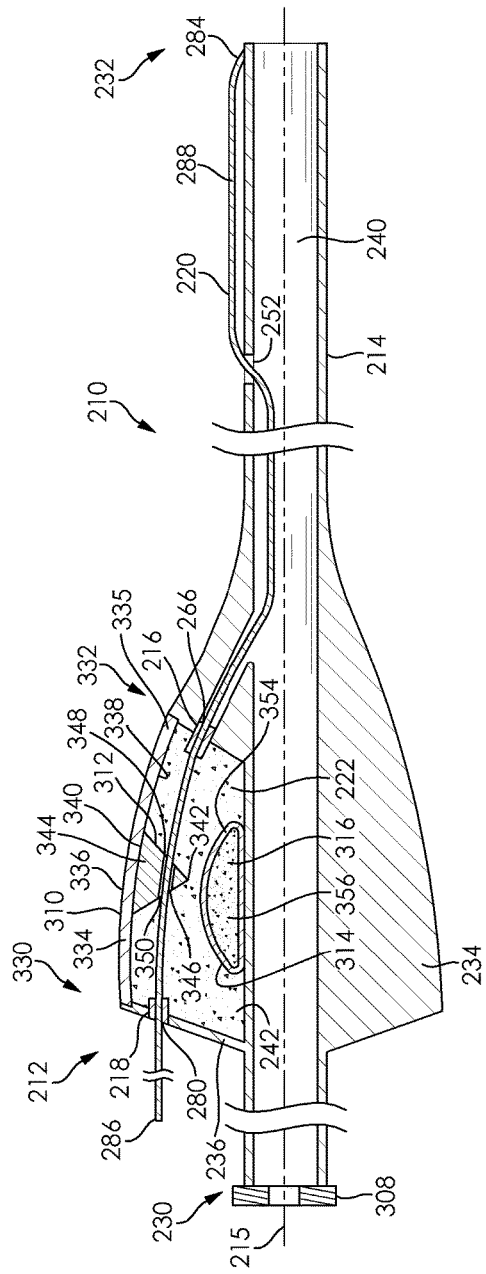
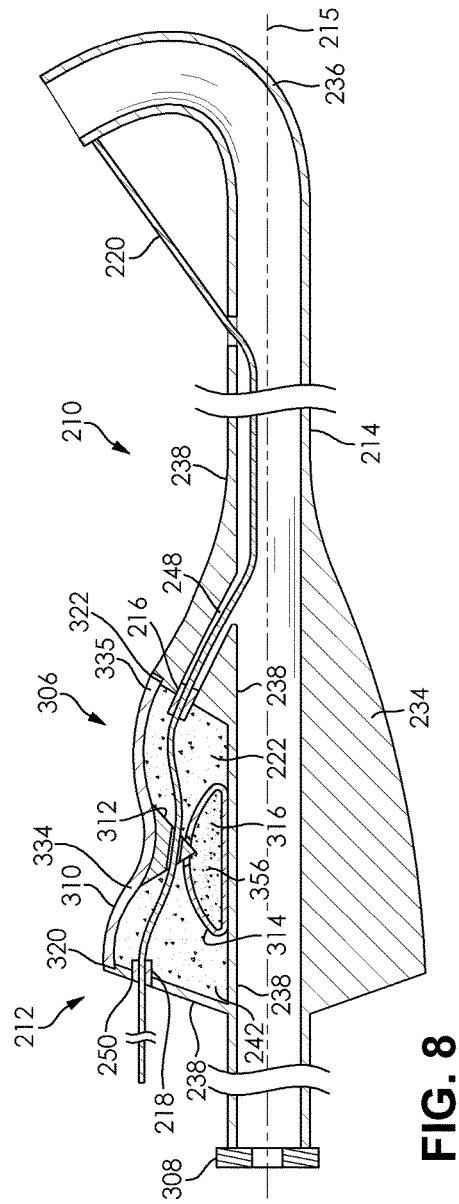
FIG. 7
FIG. 8

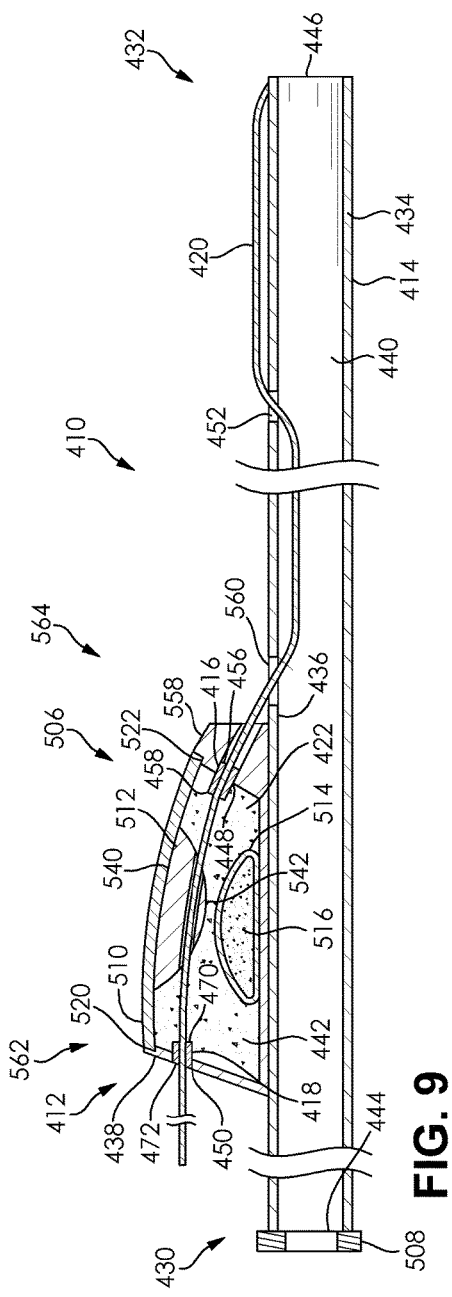

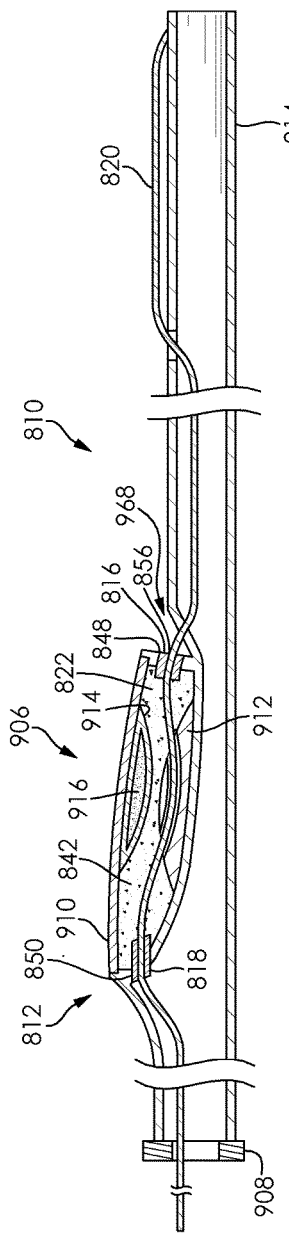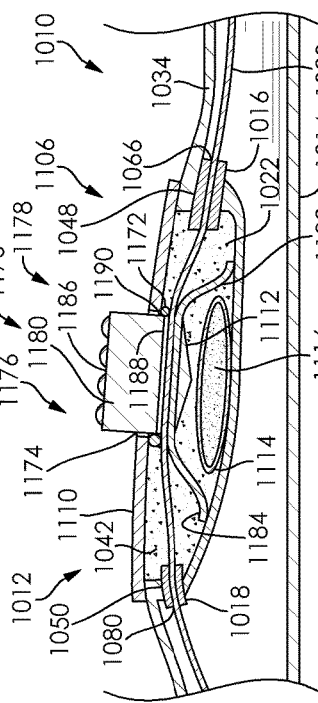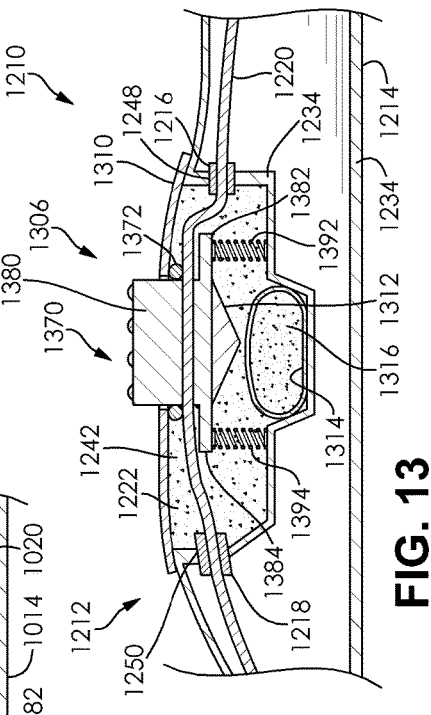
FIG. 11
FIG. 12
FIG. 13

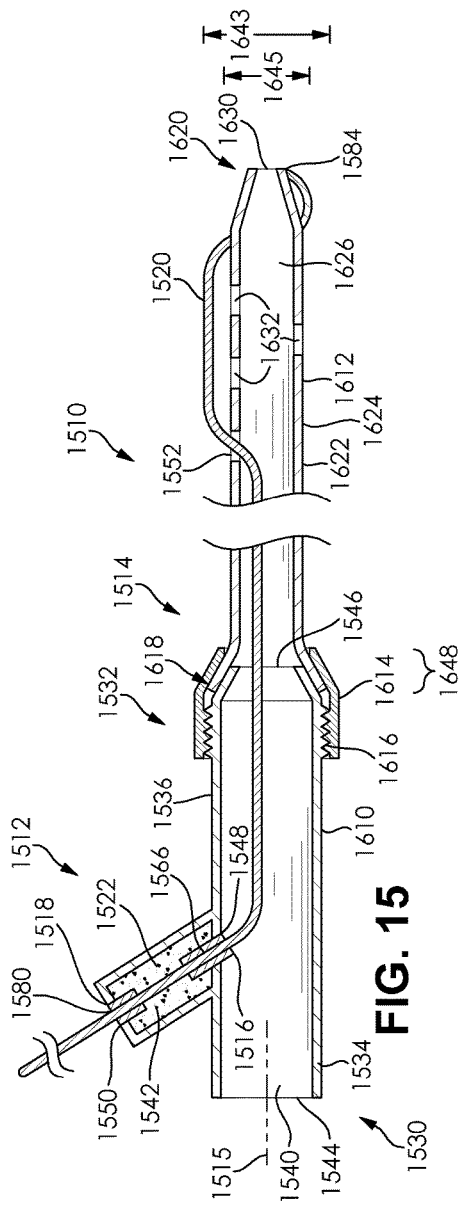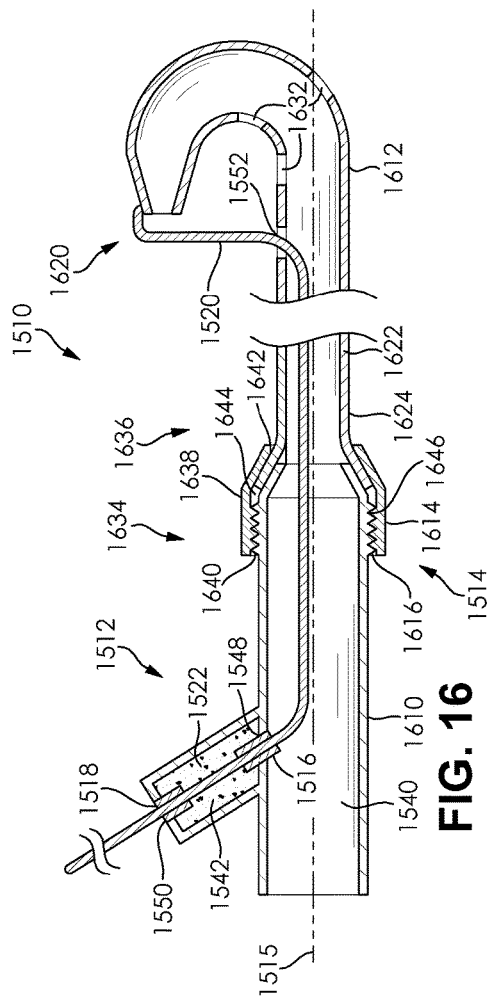

TENSION MEMBER SEAL AND SECURING MECHANISM FOR MEDICAL DEVICES

RELATED APPLICATION

This application claims the benefit of U.S. Provisional Application No. 62/036,764, filed Aug. 13, 2014. The entire disclosure of this related application is hereby incorporated into this disclosure by reference.

FIELD

The disclosure relates generally to the field of medical devices and methods of treatment.

BACKGROUND

A variety of medical devices have been developed that include a deflectable tip, which provides a mechanism for manipulating the configuration of the medical device during treatment. For example, medical devices have been developed that utilize a suture attached to an elongate member to deflect the tip of the elongate member during treatment. The suture is positioned along an exterior surface of the elongate member such that a user can grasp it to deflect the tip of the elongate member. This structural arrangement of current devices presents various drawbacks. For example, fluids disposed within a bodily passage, or the elongate member, can travel along the suture and outside of the bodily passageway as the suture is pulled to accomplish deflection. In addition, to avoid movement of tip the during treatment, these devices require that the user maintain the position of the suture once the desired tip deflection has been achieved. Therefore, a need exists for improved medical devices that include a deflectable tip.

BRIEF SUMMARY OF SELECTED EXAMPLE EMBODIMENTS

A first example embodiment of a medical device comprises an elongate member, a first plug, a second plug, a tension member, and a first material. The elongate member has a proximal end, a distal end, and an elongate member body that defines an elongate member lumen, a first chamber, a first passageway, and a second passageway. The first passageway provides access between an environment exterior to the first chamber and the first chamber. The second passageway provides access between the first chamber and an environment exterior to the first chamber. The elongate member is movable between a first configuration and a second configuration that defines a curve. The first plug is disposed within the first passageway and has a first plug body that defines a first plug passageway. The second plug is disposed within the second passageway and has a second plug body that defines a second plug passageway. The tension member has a first end and a second end. The first end is attached to the elongate member. The tension member extends from the first end, through the first plug passageway, through the first chamber, and through the second plug passageway. The tension member is movable between a first position and a second position such that when the tension member is in the first position the elongate member is in the first configuration and when the tension member is in the second position the elongate member is in the second configuration. The first material is disposed within the first chamber and is configured to seal the first chamber such that fluid is prevented from moving through the first chamber as the tension member is moved between its first position and second position.

A second example embodiment of a medical device comprises an elongate member, a first plug, a second plug, a flexible member, a tension member, a cutting element, a membrane, a first material, and a second material. The elongate member has a proximal end, a distal end, and an elongate member body that defines an elongate member lumen, a first chamber wall, a first passageway, and a second passageway. The first passageway provides access between an environment exterior to the first chamber and the first chamber. The second passageway provides access between the first chamber and an environment exterior to the first chamber. The elongate member is movable between a first configuration and a second configuration that defines a curve. The first plug is disposed within the first passageway and has a first plug body that defines a first plug passageway. A portion of the first plug extends into the elongate member lumen. The second plug is disposed within the second passageway and has a second plug body that defines a second plug passageway. The flexible member is attached to the elongate member and has a flexible member body that defines a second chamber wall that cooperatively defines a first chamber with the first chamber wall. The flexible member is movable between a first position and a second position. The tension member has a first end and a second end. The first end is attached to the elongate member. The tension member extends from the first end, through the first plug passageway, through the first chamber, and through the second plug passageway. The tension member is movable between a first position and a second position such that when the tension member is in the first position the elongate member is in the first configuration and when the tension member is in the second position the elongate member is in the second configuration. The cutting element is attached to the flexible member and disposed within the first chamber. The membrane is disposed within the first chamber and defines a second chamber within the first chamber. The membrane separates the second chamber from the first chamber when the flexible member is in the first position and the cutting element damages the membrane when the flexible member is in the second position such that the second chamber is in fluid communication with the first chamber. The first material is disposed within the first chamber and is configured to seal the first chamber such that fluid is prevented from moving through the first chamber as the tension member is moved between its first position and second position. The second material is disposed within the second chamber. The second material is separated from the first material when the flexible member is in the first position. The second material is in fluid communication with the first material when the flexible member is in the second position.

A third example embodiment of a medical device comprises an elongate member, a first plug, a second plug, a flexible member, a tension member, a cutting element, a membrane, a first material, and a second material. The elongate member has a proximal end, a distal end, and an elongate member body that defines an elongate member lumen, a first chamber wall, a first passageway, and a second passageway. The first passageway provides access between an environment exterior to the first chamber and the first chamber. The second passageway provides access between the first chamber and an environment exterior to the first chamber. The elongate member is movable between a first configuration and a second configuration that defines a curve. The first plug is disposed within the first passageway and has a first plug body that defines a first plug passageway in communication with the elongate member lumen. A portion of the first plug extends into the elongate member lumen. The second plug is disposed within the second passageway and has a second plug body that defines a second plug passageway. The flexible member is attached to the elongate member and has a flexible member body that defines a second chamber wall that cooperatively defines a first chamber with the first chamber wall. The flexible member is movable between a first position and a second position. The tension member has a first end and a second end. The first end is attached to the elongate member. The tension member extends from the first end, through the first plug passageway, through the first chamber, and through the second plug passageway. The tension member is movable between a first position and a second position such that when the tension member is in the first position the elongate member is in the first configuration and when the tension member is in the second position the elongate member is in the second configuration. The cutting element is attached to the flexible member and disposed within the first chamber. The membrane is disposed within the first chamber and defines a second chamber within the first chamber. The membrane separates the second chamber from the first chamber when the flexible member is in the first position and the cutting element damages the membrane when the flexible member is in the second position such that the second chamber is in fluid communication with the first chamber. The first material is disposed within the first chamber and is configured to seal the first chamber such that fluid is prevented from moving through the first chamber as the tension member is moved between its first position and second position. The first material comprises a first part of a liquid hardenable solution. The second material is disposed within the second chamber. The second material is separated from the first material when the flexible member is in the first position. The second material is in fluid communication with the first material when the flexible member is in the second position. The second material comprises a second part of a liquid hardenable solution.

BRIEF DESCRIPTION OF THE DRAWINGS

FIG. 1 is a partially broken away side view of an example embodiment of a medical device that includes a tension member seal. The medical device is shown in a first configuration.

FIG. 2 is a partially broken away side view of the medical device illustrated in FIG. 1 in a second configuration.

FIG. 7 is a partially broken away sectional view of the medical device illustrated in FIG. 5 taken along the lengthwise axis of the elongate member. The medical device is shown in a first configuration.

FIG. 8 is a partially broken away sectional view of the medical device illustrated in FIG. 5 taken along the lengthwise axis of the elongate member. The medical device is shown in a second configuration.

FIG. 9 is a partially broken away sectional view of another example embodiment of a medical device taken along the lengthwise axis of the elongate member. The medical device includes a tension member seal and securing mechanism and is shown in the first configuration.

FIG. 10 is a partially broken away sectional view of another example embodiment of a medical device taken along the lengthwise axis of the elongate member. The medical device includes a tension member seal and securing mechanism and is shown in the first configuration.

FIG. 11 is a partially broken away sectional view of another example embodiment of a medical device taken along the lengthwise axis of the elongate member. The medical device includes a tension member seal and securing mechanism and is shown in the first configuration.

FIG. 12 is a partial sectional view of another example embodiment of a medical device taken along the lengthwise axis of the elongate member. The medical device includes a tension member seal and securing mechanism and is shown in the first configuration.

FIG. 13 is a partial sectional view of another example embodiment of a medical device taken along the lengthwise axis of the elongate member. The medical device includes a tension member seal and securing mechanism and is shown in the first configuration.

FIG. 15 is a partially broken away sectional view of another example embodiment of a medical device taken along the lengthwise axis of the elongate member. The medical device includes a tension member seal and is shown in a first configuration.

FIG. 16 is a partially broken away sectional view of the medical device illustrated in FIG. 15 taken along the lengthwise axis of the elongate member. The medical device is shown in a second configuration.

DETAILED DESCRIPTION

Figure 4:
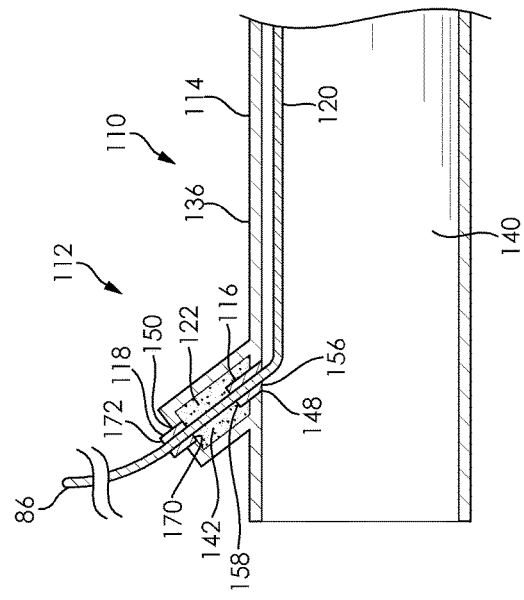
FIG. 4 is a partial sectional view of another example embodiment of a medical device taken along the lengthwise axis of the elongate member. The medical device includes a tension member seal.

The following detailed description and the appended drawings describe and illustrate various example embodiments of medical devices that include a tension member seal, medical devices that include a tension member seal and securing mechanism, and methods of treatment. The description and illustration of these examples are provided to enable one skilled in the art to make and use a medical device that includes a tension member seal, medical devices that include a tension member seal and securing mechanism, and to practice a method of treatment using a medical device. They are not intended to limit the scope of the claims in any manner. The various example embodiments of medical devices that include a tension member seal and medical devices that include a tension member seal and securing mechanism can be used for any suitable purpose, such as a drainage catheter, delivery device, or any other device in which the inclusion of a tension member seal and/or securing mechanism is considered desirable.

The use of "e.g.," "etc.," "for instance," "in example," and "or," and grammatically related terms, indicate non-exclusive alternatives without limitation, unless otherwise noted. The use of "optionally," and grammatically related terms, means that the subsequently described element, event, feature, or circumstance may or may not be present or occur, and that the description includes instances where said element, event, feature, or circumstance occurs and instances where it does not. The use of "attached," and grammatically related terms, refers to the fixed, releasable, or integrated association of two or more elements and/or devices, unless otherwise noted. Thus, the term "attached" includes releasably attaching or fixedly attaching two or more elements and/or devices, unless otherwise noted. As used herein, the terms "proximal" and "distal" are used to describe opposing axial ends of the particular element or feature being described. The use of "diameter" refers to the length of a straight line passing from side to side through the center of a body, element, or feature, and does not impart any structural configuration on the body, element, or feature. The use of "circumference" refers to the distance around the exterior surface of a body, element, or feature, and does not impart any structural configuration on the body, element, or feature. The use of "bodily passage" or "body passage" refers to any passage within the body of an animal, including humans, and includes elongate passages, arteries, veins, the urinary tract, chambers, cavities, and abscesses. The term "coil" refers to a length of an element that is arranged in one or more complete or partial spirals, loops, and/or rings. The term "coil" does not require regularity in the arrangement of the one or more spirals, loops, and/or rings and does not require that an entire spiral, loop, and/or ring be formed.

The term "to damage," and grammatically related terms, refers to the act of shattering, cracking, breaking, fracturing, fragmenting, puncturing, penetrating, ripping, tearing, rupturing, and/or perforating a body, element, or feature, or a portion of a body, element, or feature or a body, element, or feature, or a portion of a body, element, or feature, becoming shattered, cracked, broken, fractured, fragmented, punctured, penetrated, ripped, torn, ruptured, and/or perforated.

Figure 3:
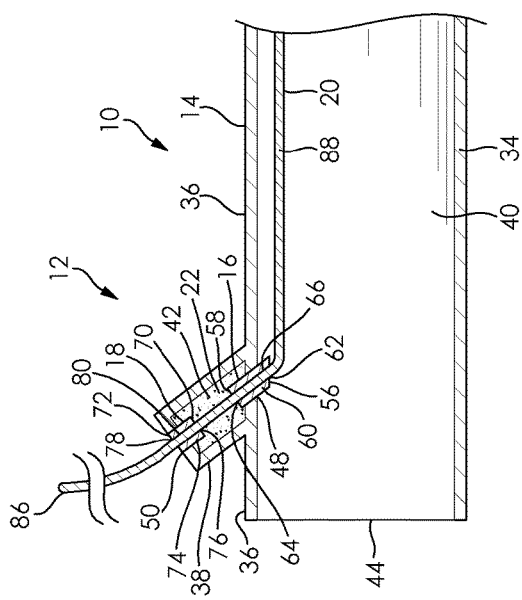
FIG. 3 is a partial sectional view of the medical device illustrated in FIG. 1 taken along the lengthwise axis of the elongate member.
Figure 6:
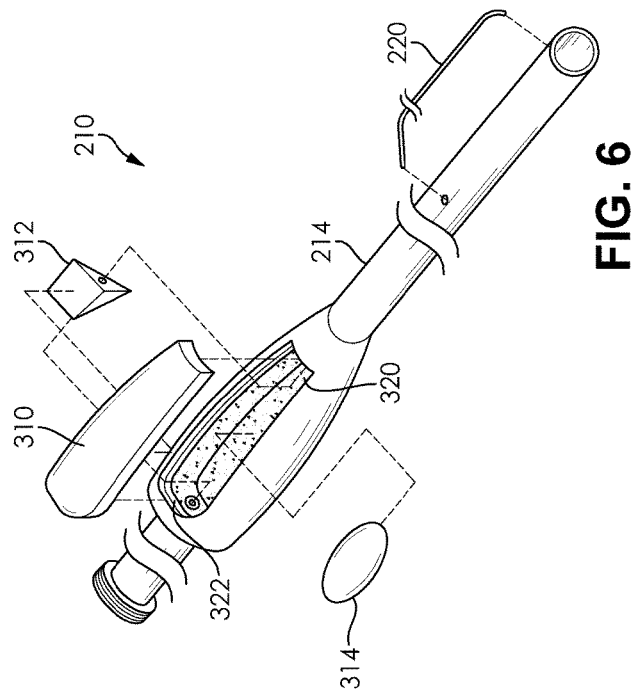
FIG. 6 is a partially broken away exploded view of the medical device illustrated in FIG. 5.
Figure 5:
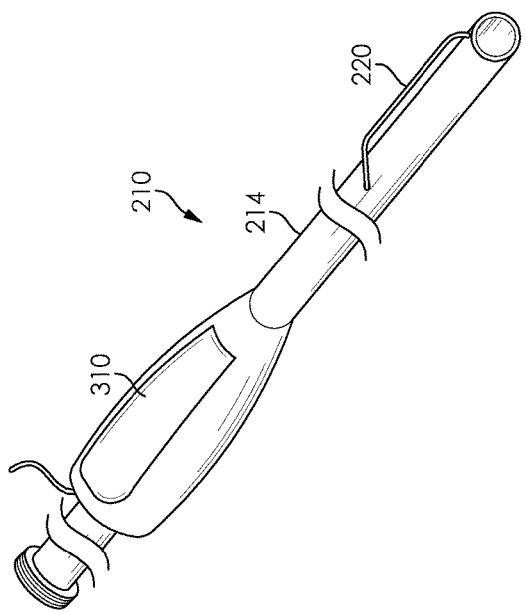
FIG. 5 is a partially broken away perspective view of an example embodiment of a medical device that includes a tension member seal and securing mechanism. The medical device is shown in a first configuration.

FIGS. 1, 2, and 3 illustrate an example embodiment of a medical device 10 that includes a tension member seal 12. The medical device 10 has an elongate member 14, a first plug 16, a second plug 18, a tension member 20, and a material 22 disposed within a portion of the elongate member 14. The medical device 10 is movable between a first configuration, as shown in FIG. 1, and a second configuration, as shown in FIG. 2.

In the illustrated embodiment, the elongate member 14 has a lengthwise axis 15, a proximal end 30, a distal end 32, and an elongate member body 34 that defines a wall 36, an elongate member lumen 40, a chamber 42, a first opening 44, a second opening 46, a first passageway 48, a second passageway 50, and a third passageway 52. The first opening 44 is defined on the proximal end 30 and the second opening 46 is defined on the distal end 32. The elongate member lumen 40 extends from the first opening 44 to the second opening 46 and is defined by the wall 36.

A portion of the wall 36 of the elongate member 14 extends away from the lengthwise axis 15 of the elongate member 14 and defines the chamber 42, which is sized and configured to receive material 22, as described in more detail herein. The first passageway 48 extends through the wall 36 between the proximal end 30 and the distal end 32 of the elongate member 14 and provides access between an environment exterior to the chamber 42 and the chamber 42. In the illustrated embodiment, the first passageway 48 provides access between the elongate member lumen 40 and the chamber 42 and is in communication with the elongate member lumen 40 and the chamber 42. In the illustrated embodiment, the first passageway 48 has a diameter that is sized and configured to receive the first plug 16 and the tension member 20, as described in more detail herein.

The second passageway 50 extends through the wall 36 and provides access between the chamber 42 and an environment exterior to the chamber 42. In the illustrated embodiment, the second passageway 50 provides access between the chamber 42 and the environment exterior to the elongate member lumen 40 and is in communication with the chamber 42 and the environment exterior to the elongate member lumen 40. In the illustrated embodiment, the second passageway 50 has a diameter that is sized and configured to receive the second plug 18 and the tension member 20, as described in more detail herein. In the embodiment illustrated, the first passageway 48 is disposed on a first axis and the second passageway 50 is disposed on a second axis that is coaxial with the first axis. However, alternative embodiments can include first passageway that is disposed on a first axis and second passageway that is disposed on a second axis that is not coaxial with the first axis.

The third passageway 52 extends through the wall 36 and is disposed between the proximal end 30 and the distal end 32 of the elongate member 14. In the illustrated embodiment, the third passageway 52 is disposed between the first passageway 48 and the distal end 32 of the elongate member 14. The third passageway 52 is sized and configured to receive a portion of the tension member 20 such that the tension member 20 can be moved between its first and second positions, as described in more detail herein.

The elongate member 14 is movable between a first configuration, as shown in FIG. 1, in which the elongate member 14 is substantially straight and a second configuration, as shown in FIG. 2, in which the elongate member 14 is curved and defines a curve 54 between its proximal end 30 and distal end 32. In the first configuration, the outer surface of the elongate member 14 is substantially parallel to the lengthwise axis 15 of the elongate member 14 (e.g., the elongate member 14 is substantially straight). In the second configuration, a proximal portion of the outer surface of the elongate member 14 is parallel to the lengthwise axis 15 of the elongate member 14 (e.g., is substantially straight) and a distal portion of the outer surface of the elongate member 14 is not parallel to the lengthwise axis 15 of the elongate member 14 such that the distal portion of the elongate member 14 is curved. However, alternative embodiments can include elongate members that are configured to move between a first configuration in which the elongate member is straight, or substantially straight, such that the elongate member defines a first radius of curvature in the first configuration (e.g., a distal portion of the outer surface is not parallel to the lengthwise axis of the elongate member, a distal portion of the outer surface is substantially parallel to the lengthwise axis of the elongate member) and a second configuration in which the elongate member is curved such that a distal portion of the elongate member defines a second radius of curvature in the second configuration that is less than the first radius of curvature (e.g., the distal portion of the outer surface is not parallel to the lengthwise axis of the elongate member).

While the elongate member 14 has been illustrated as having a particular structural configuration, an elongate member included in a medical device can have any suitable structural configuration. Skilled artisans will be able to select a suitable configuration for an elongate member that is intended to be included in a medical device according to a particular embodiment based on various considerations, including the treatment intended to be performed. For example, elongate members that are configured to define a single curve, multiple curves, a coil, and/or one or more coils, along their lengths can be used to form a medical device, such as those described herein. While elongate member 14 has been illustrated as defining a first passageway 48, a second passageway 50, and a third passageway 52, an elongate member can defined any suitable number of passageways that are sized and configured to receive a portion of a tension member and/or plug. Example number of passageways considered suitable for an elongate member to define include one, at least one, two, a plurality, three, four, five, six, and any other number considered suitable for a particular embodiment. For example, a medical device can include an elongate member that omits the inclusion of a third passageway such that a tension member included in the medical device has a first end attached within the elongate member lumen, or on the outer surface of an elongate member, at, or near, the distal end of the elongate member or between the proximal and distal ends of the elongate member. Alternative to an elongate member defining a chamber, a separate member that defines a chamber can be attached to an elongate member such that the chamber is in communication with the elongate member lumen and/or an environment exterior to the elongate member lumen.

The elongate member 14 can optionally include a connector or adaptor on its proximal end 30 that provides a mechanism for attaching another device, such as a suction device, to the elongate member 14. Any suitable connector or adapter capable of attaching one or more devices to the elongate member 14 can be used. Skilled artisans will be able to select a suitable connector or adapter to include on an elongate member according to a particular embodiment based on various considerations, including the material(s) that forms the elongate member. Example connectors or adapters considered suitable to include on an elongate member include threaded connectors, Tuohy Borst adapters, luer lock connectors, conical connectors (e.g., cones, sockets), and any other connector or adapter considered suitable for a particular embodiment.

The elongate member 14 can have any suitable outside diameter and any suitable length, and skilled artisans will be able to select a suitable outside diameter and length for an elongate member according to a particular embodiment based on various considerations, including the desired bodily passage within which a medical device is intended to be used. Example diameters and lengths considered suitable include those that are capable of being introduced into a bodily passage such that the bodily passage can be drained or otherwise treated.

The elongate member 14 can be formed of any suitable material and can be fabricated using any suitable method or technique. Skilled artisans will be able to select a suitable material to form an elongate member and a suitable method or technique to fabricate an elongate member according to a particular embodiment based on various considerations, including the desired flexibility of the elongate member. Example materials considered suitable to form an elongate member include biocompatible materials, materials that can be made biocompatible, metals such as stainless steel, titanium, nickel-titanium alloy (e.g., Nitinol), polymers, Pebax (Pebax is a registered trademark of AtoChimie Corporation of Allee des Vosges, Courbevoie, France), nylon, polyethylene, polyurethane, silicone, coiled materials, braided materials, combinations of the materials described herein, and any other material considered suitable for a particular application. Example methods and techniques considered suitable to fabricate an elongate member include extrusion processes, molding processes, injection molding processes, and any other method or technique considered suitable for a particular embodiment.

Any suitable structure, or combination of components, can be used to form a tension member seal included in a medical device and selection of a suitable structure, or combination of components, to form a tension member seal can be based on various considerations, including the structural configuration of an elongate member included in a medical device of which the tension member seal is a component. Examples of tension member seals considered suitable for inclusion in a medical device include tension members seals that include only a first plug, only a second plug, more than two plugs, omit the inclusion of a first or second material, and any other tension member seal considered suitable for a particular embodiment.

In the illustrated embodiment, an example of a suitable tension member seal 12 comprises the first plug 16 disposed within the first passageway 48 defined by the elongate member 14, the second plug 18 disposed within the second passageway 50 defined by the elongate member 14, and the material 22 disposed within the chamber 42. However, alternative embodiments can include a tension member seal that comprises one or more of these components and/or additional components. The first plug 16 is disposed within the first passageway 48 and has a first end 56, a second end 58, and a first plug body 60 that defines a first plug first opening 62, a first plug second opening 64, a first plug passageway 66, and a first plug length that extends from the first end 56 to the second end 58. The first plug passageway 66 extends from the first plug first opening 62 to the first plug second opening 64. The first plug 16 has an outside diameter that is equal to the diameter of the first passageway 48. However, alternative embodiments can include a first plug that has an outside diameter that is less than the diameter of the first passageway, or greater than the diameter of the first passageway such that a friction fit between the elongate member and the first plug can be achieved. The first plug first opening 62 is in communication with an environment exterior to the chamber 42 and the first plug second opening 64 is in communication with the chamber 42. In the illustrated embodiment, each of the first plug first opening 62 and the first plug passageway 66 is in communication with the elongate member lumen 40.

In the illustrated embodiment, the first plug 16 partially extends into the elongate member lumen 40 such that the first end 56 of the first plug 16, and a portion of the length of the first plug 16, is disposed within the elongate member lumen 40. This structural arrangement provides a mechanism to reduce contact between the tension member 20 and the elongate member 14 during use. The first plug 16 partially extends into the chamber 42 such that the second end 58 of the first plug 16, and a portion of the length of the first plug 16, is disposed within the chamber 42. This structural configuration provides a mechanism to direct the tension member 20 toward the second plug 18. However, alternative embodiments can include a first plug that does not partially extend into an elongate member lumen (e.g., a first plug has a first end that is flush with the inner surface of the elongate member that defines the elongate member lumen), a first plug that has a first end that is disposed within a passageway defined by the elongate member, a first plug that does not partially extend into a chamber (e.g., a first plug has a second end that is flush within the inner surface of the elongate member that defines the chamber), and/or a first plug that has a second end that is disposed within a passageway defined by the elongate member.

The second plug 18 is disposed within the second passageway 50 and has a first end 70, a second end 72, and a second plug body 74 that defines a second plug first opening 76, a second plug second opening 78, a second plug passageway 80, and a second plug length that extends from the first end 70 to the second end 72. The second plug passageway 80 extends from the second plug first opening 76 to the second plug second opening 78. The second plug 18 has an outside diameter that is equal to the diameter of the second passageway 50. However, alternative embodiments can include a second plug that has an outside diameter that is less than the diameter of the second passageway, or greater than the diameter of the second passageway such that a friction fit between the elongate member and the second plug can be achieved. The second plug first opening 76 is in communication with the chamber 42 and the second plug second opening 78 is in communication with an environment exterior to the chamber 42. In the illustrated embodiment, each of the second plug second opening 78 and the second plug passageway 80 is in communication with an environment exterior to the elongate member lumen 40.

In the illustrated embodiment, the second plug 18 partially extends into the chamber 42 such that the first end 70 of the second plug 18, and a portion of the length of the second plug 18, is disposed within chamber 42. This structural arrangement provides a mechanism to direct the tension member 20 toward the first plug 16. The second end 72 of the second plug 18 is flush with the outer surface of the wall 36. However, alternative embodiments can include a second plug that does not partially extend into a chamber (e.g., a second plug has a first end that is flush within the inner surface of the elongate member that defines the chamber), a second plug that has a first end that is disposed within a passageway defined by the elongate member, a second plug that partially extends into an environment exterior to the chamber, and/or a second plug that has a second end that is disposed within a passageway defined by the elongate member.

The first plug 16 is configured to prevent the material 22 disposed within the chamber 42 from exiting the chamber 42 as the tension member 20 is moved between its first and second positions and prevents fluid that has been introduced into the elongate member lumen 40 from passing through the first plug 16 and into the chamber 42. For example, the first plug 16 is configured to prevent the material 22 from being transferred from within the chamber 42 to an environment exterior to the chamber 42 (e.g., the elongate member lumen 40) on the tension member 20 as it is moved between its first and second positions and prevents fluids that enter the elongate member lumen 40 from escaping through the chamber 42. The second plug 18 is configured to prevent the material 22 disposed within the chamber 42 from exiting the chamber 42 as the tension member 20 is moved between its first and second positions and prevents fluid from passing through the second plug 18 into the chamber 42. For example, the second plug 18 is configured to prevent the material 22 from being transferred from within the chamber 42 to an environment exterior to the chamber 42 on the tension member 20 as it is moved between its first and second positions.

In the embodiment illustrated, the passageway 66 defined by the first plug 16 is disposed on a first axis and the passageway 80 defined by the second plug 18 is disposed on a second axis that is coaxial with the first axis. However, alternative embodiments can include a first plug that defines a passageway disposed on a first axis and a second plug that defines a passageway that is disposed on a second axis that is not coaxial with the first axis.

In the illustrated embodiment, each of the first plug passageway 66 and the second plug passageway 80 is preformed and sized and configured to receive a portion of the tension member 20 such that the tension member 20 can be moved between its first and second positions through the first plug passageway 66 and the second plug passageway 80. Preforming the passageways 66, 80 can be accomplished using any suitable method or technique, such as by forming the passageways within a mold or creating the passageways subsequent to fabricating the plugs (e.g., drilling the passageways through the plugs, passing a needle through a plug). In the illustrated embodiment, each of the first plug passageway 66 and second plug passageway 80 has an inside diameter that is smaller than the outside diameter of the tension member 20 when the tension member 20 is not disposed within the first passageway 66 or second passageway 80. This structural arrangement forms a sealing engagement between the tension member 20 and the first plug 16 and second plug 18 when the medical device 10 is assembled. However, alternative embodiments can include a first plug passageway and/or a second plug passageway that has an inside diameter that is equal to, substantially equal to, or greater than the outside diameter of a tension member.

Each of the first plug 16 and second plug 18 can be attached to the elongate member 14 using any suitable technique or method of attachment. Skilled artisans will be able to select a suitable technique or method of attachment between a plug and an elongate member according to a particular embodiment based on various considerations, including the material(s) that form the plug and/or the elongate member. Example techniques and methods of attachment between a plug and an elongate member considered suitable include using adhesives, threaded connections, morse tapers, friction fit configurations, snap fit configurations, combinations of those described herein, and any other technique or method considered suitable for a particular embodiment. In the illustrated embodiment, the first plug 16 and the second plug 18 are attached to the elongate member 14 using an adhesive and a friction fit between the first plug 16 and the elongate member 14 and a friction fit between the second plug 18 and the elongate member 14. However, alternative embodiments can include a first plug that is attached to an elongate member using a first technique or method and a second plug that is attached to the elongate member using a second technique or method that is different than the first technique or method.

Each of the first plug 16 and second plug 18 can be formed of any suitable material, can be fabricated using any suitable method or technique, and can have any suitable length. Skilled artisans will be able to select a suitable material to form a plug, a suitable method or technique to fabricate a plug, and a suitable length for a plug included in a medical device according to a particular embodiment based on various considerations, including the desired flexibility of the plug. Example materials considered suitable to form a plug include biocompatible materials, materials that can be made biocompatible, polymers, elastomeric materials, Pebax (Pebax is a registered trademark of AtoChimie Corporation of Allee des Vosges, Courbevoie, France), nylon, polyethylene, polyurethane, silicone, rubber, flexible materials (e.g., materials that are relatively more flexible than the material that forms an elongate member of a medical device), compliant materials, compressible materials (e.g., materials that can be compressed by an average human without using any tools, materials that can be compressed by a human using hand tools), and any other material considered suitable for a particular application. While not required to form a plug included in a medical device, flexible materials are considered advantageous at least because their flexible nature may reduce the friction between a plug and a tension member during movement of the tension member. In the illustrated embodiment, the first plug 16 is formed of a first material and the second plug 18 is formed of a second material that is the same as the first material. In the embodiment shown, the first material and the second material are silicone. However, alternative embodiments can include a first plug that is formed of a first material and a second plug that is formed of a second material that is different than the first material. Example methods and techniques considered suitable to fabricate a plug include extrusion processes, molding processes, and any other method or technique considered suitable for a particular application. In the illustrated embodiment, the first plug has a first length and the second plug has a second length that is less than the first length. However, alternative embodiments can include a first plug that has a first length and a second plug that has a second length that is equal to, substantially equal to, or greater than, the first length.

In the illustrated embodiment, the elongate member 14 is formed of a first material and each of the first plug 16 and second plug 18 is formed of a second material. The first material is different than the second material. However, alternative embodiments can include an elongate member that is formed of a first material that is the same as the material that forms the first plug and/or the second plug.

The tension member 20 has a first end 84, a second end 86, and a body 88. The first end 84 is attached to the wall 36 near the distal end 32 of the elongate member 14 and the second end 86 is free of attachment to the elongate member 14. In the embodiment illustrated, the tension member 20 has an outside diameter that is greater than the inside diameter of the first plug passageway 66 and the second plug passageway 80. However, the outside diameter of a tension member can be greater than, less than, equal to, or substantially equal to, the inside diameter of a first plug passageway and/or second plug passageway. The tension member 20 extends from the first end 84, along a portion of the outer surface of the elongate member 14, through the third passageway 52 and into the elongate member lumen 40, through a portion of the elongate member lumen 40, through the first plug passageway 66, through the chamber 42, and through the second plug passageway 80. The tension member 20 is movable between a first position and a second position such that when the tension member 20 is in the first position the elongate member 14 is in the first configuration and when the tension member 20 is in the second position the elongate member 14 is in the second configuration.

While the tension member 20 has been illustrated as having a first end 84 attached to the wall 36 near the distal end 32 of the elongate member 14 and disposed in a particular configuration on the elongate member 14, a tension member can be attached to an elongate member at any suitable location and positioned in any suitable manner on an elongate member such that it is configured to move the elongate member between the first configuration and second configuration. Skilled artisans will be able to select a suitable configuration to position a tension member according to a particular embodiment based on various considerations, such as the structural arrangement of an elongate member included in a medical device in which the tension member is a component and/or the number of curves intended to be defined by the elongate member when it is in the second configuration. For example, the tension member can be attached at any suitable location on an elongate member (e.g., at the distal end, proximal to the distal end, between the proximal end and the distal end of the elongate member), can extend through any suitable number of passageways defined by an elongate member, through any suitable number of passageways defined by a plug, through any suitable number of lumens defined by an elongate member, along any suitable portion of the outer surface and/or inner surface of an elongate member, can extend from a first end to a plug only along an outer surface of an elongate member, and/or can extend from a first end to a plug only along an inner surface of an elongate member.

The tension member 20 can be formed of any suitable material and can have any suitable length, stiffness, and any suitable cross-sectional configuration. Skilled artisans will be able to select a suitable material to form a tension member and a suitable length, cross-sectional configuration, and stiffness for a tension member according to a particular embodiment based on various considerations, including the material(s) that forms an elongate member and/or a plug included in a medical device of which the tension member is a component. Example materials considered suitable to form a tension member include biocompatible materials, materials that can be made biocompatible, biological materials, polymers, nylon, polyester, polypropylene, tension members that include antimicrobial materials, polyglycolic acid, polylactic acid, polydioxanone, and any other material considered suitable for a particular application. A tension member can comprise a monofilament tension member or a multi-filament tension member. Commercially available sutures (e.g., monofilament, multi-filament), coils, thread-like structures, and lengths of wire are examples of tension members considered suitable to include in a medical device, such as those described herein. A tension member can have any suitable outside diameter. For example, the diameter of the tension member can be based on the diameter of the predefined passageway of a plug, the material disposed within a chamber, and/or the force required to move an elongate member between a first configuration and/or second configuration.

The material 22 is disposed within the chamber 42 defined by the elongate member 14 and is configured to seal the chamber 42 such that fluid, such as bodily fluid or other fluid disposed within the elongate member 14 during use of the medical device 10, is prevented from moving from an environment exterior to the chamber 42 and into and/or through the chamber 42 (e.g., through the first plug 16, second plug 18, and/or material 22) as the tension member 20 is moved between its first and second positions. The material 22 can comprise any suitable material, and skilled artisans will be able to select a suitable material to include in a chamber defined by an elongate member according to a particular embodiment based on various considerations, including the material(s) that form the elongate member, a plug, and/or a tension member included in a medical device of which the material is a component. Example materials considered suitable to include in a chamber defined by an elongate member include biocompatible materials, materials that can be made biocompatible, a first part of a liquid hardenable material, a second part of a liquid hardenable material, medical grade materials, hydrophobic materials, non-hydrophobic materials, inert materials, fluids, gels, viscous materials, viscous flowable materials, high viscosity materials, high viscosity fluids, silicone, liquid silicone, liquid silicone rubber, silicone gel, medical grade silicone (e.g., Dow-Corning 360 Medical Fluid), epoxy resins, uncured epoxy resins, a first part of an epoxy resin, a second part of an epoxy resin, epoxy hardeners, uncured epoxy hardeners, polyepoxides, polyfunctional amines, acids, phenols, alcohols, thiols, sealant materials, and any other material considered suitable for a particular embodiment.

The material 22 disposed within the chamber 42 can have any suitable viscosity, and skilled artisans will be able to select a suitable viscosity for a material disposed within a chamber of a medical device according to a particular embodiment based on various considerations, such as the diameter of the passageway defined by a plug included in a medical device of which the material is a component. The viscosity of the material 22 disposed within the chamber 42 defined by an elongate member 14 can be based on the diameter of the passageway 66 defined by the first plug 16, the diameter of the passageway 80 defined by the second plug 18, the diameter of the tension member 20, the material(s) that forms the elongate member 14, the material(s) that forms the first plug 16, the material(s) that forms the second plug 18, and/or the material(s) that forms the tension member 20. Example viscosities considered suitable for a material disposed within a chamber include materials with viscosities equal to 1000 centipoise, substantially equal to 1000 centipoise, greater than 1000 centipoise, less than 1000 centipoise, equal to 1000 centistokes, substantially equal to 1000 centistokes, greater than 1000 centistokes, less than 1000 centistokes, and any other viscosity considered suitable for a particular embodiment. In the illustrated embodiment, the material 22 comprises liquid silicone with a viscosity of 1000 centistokes.

In use, the tension member 20 has a first length disposed distal to the first plug 16 when the tension member 20 is in the first position, as shown in FIG. 1, and has a second length disposed distal to the first plug 16 when the tension member 20 is in the second position, as shown in FIG. 2. The second length is less than the first length. Movement of the tension member 20 from its first position to its second position produces tension in the tension member 20 such that the elongate member 14 moves from its first configuration to its second configuration in which elongate member 14 defines curve 54. Movement of the tension member 20 from its second position to its first position reduces, or eliminates, tension in the tension member 20 such that the elongate member 14 moves from its second configuration to its first configuration.

The length of the tension member 20 that is included in a medical device determines the range of radii of curvature that can be achieved by the elongate member 14 during use. For example, to achieve a desired radius of curvature, the tension member 20 is moved to its second position by positioning a desired length of the tension member 20 distal to the first plug 16. Once a desired radius of curvature has been achieved, the second position of the tension member 20 can be maintained using any suitable method or structure. For example, a user can maintain a desired radius of curvature in an elongate member 14 by tying a knot along the length of the tension member 20 between its first end 84 and second end 86 (e.g., proximal to the second plug 18) such that the knot is prevented from advancing into the passageway 80 defined by the second plug 18. Alternatively, a desired radius of curvature can be maintained using an actuator, locking mechanism, such as a clamp (e.g., hemostat clamp), or a securing mechanism, such as those described herein. Movement of the elongate member 14 between a first configuration and a second configuration provides a mechanism to advance the medical device 10 through tortuous bodily passages during the performance of a procedure.

An example method of assembling the medical device 10 comprises passing the tension member 20 through the passageway 66 defined by the first plug 16. Subsequently, the first plug 16 can be inserted into the first passageway 48 defined by the elongate member 14 and attached within the first passageway 48. The chamber 42 defined by the elongate member 14 can then be entirely filled with the material 22. Alternative embodiments, however, can include medical devices that have an elongate member that defines a chamber that is partially filled with material. The tension member 20 can be passed through the passageway 80 defined by the second plug 18 prior to the chamber 42 being filled with the material 22 or subsequent to the chamber 42 being filled with the material 22. After the tension member 20 has been passed through the passageway 80 defined by the second plug 18 and the chamber 42 has been filled with the material 22, the second plug 18 can be inserted into the second passageway 50 defined by the elongate member 14 and attached within the second passageway 50. The chamber 42 is sealed when the second plug 18 is attached within the second passageway 50. The tension member 20 can be passed through the third passageway 52 at any suitable time and the first end 84 of the tension member 20 can be attached to the elongate member 14 at any suitable time.

FIG. 4 illustrates another example embodiment of a medical device 110. The medical device 110 is similar to the medical device 10 illustrated in FIGS. 1, 2, and 3 and described above, except as detailed below. The medical device 110 comprises a tension member seal 112, an elongate member 114, a first plug 116, a second plug 118, a tension member 120, and a material 122 disposed within a portion of the elongate member 114. The medical device 110 is movable between a first configuration and a second configuration. In the embodiment shown, the tension member seal 112 comprises the first plug 116 disposed within the first passageway 148, the second plug 118 disposed within the second passageway 150, and the material 122 disposed within the chamber 142.

In the illustrated embodiment, the first plug 116 is disposed within the first passageway 148 such that the first end 156 of the first plug 116 is flush with the wall 136 that defines the elongate member lumen 140 and the second end 158 of the first plug 116 is disposed within the chamber 142 defined by the elongate member 114. In addition, the second plug 118 is disposed within the second passageway 150 such that the first end 170 of the second plug 118 is flush with the wall 136 and the second end 172 of the second plug 118 is disposed in an environment exterior to the chamber 142.

FIGS. 5, 6, 7, and 8 illustrate another example embodiment of a medical device 210. The medical device 210 is similar to the medical device 10 illustrated in FIGS. 1, 2, and 3 and described above, except as detailed below. The medical device 210 comprises a tension member seal 212, an elongate member 214, a first plug 216, a second plug 218, a tension member 220, and a first material 222 disposed within a portion of the elongate member 214. The medical device 210 is movable between a first configuration and a second configuration. In the embodiment shown, the tension member seal 212 comprises the first plug 216 disposed within the first passageway 248, the second plug 218 disposed within the second passageway 250, and the material 222 disposed within the first chamber 242.

In the illustrated embodiment, the medical device 210 includes a tension member securing mechanism 306, connector 308, a flexible member 310, a cutting element 312, a membrane 314, and a second material 316 disposed within the membrane 314. Any suitable structure, or combination of components, can be used to form a securing mechanism included in a medical device and selection of a suitable structure, or combination of components, to form a securing mechanism can be based on various considerations, including the structural configuration of an elongate member included in a medical device of which the securing mechanism is a component. Examples of securing mechanisms considered suitable for inclusion in a medical device include securing mechanisms that include more than one membrane, each membrane containing a first or second material, securing mechanisms that omit the inclusion of a flexible member, a cutting element, a membrane, and/or a second material, and any other securing mechanism considered suitable for a particular embodiment.

In the illustrated embodiment, an example of a suitable tension member securing mechanism 306 comprises the first material 222 disposed within the first chamber 242 defined by the elongate member 214, the flexible member 310 attached to the elongate member 214, the cutting element 312 attached to the flexible member 310, the membrane 314 disposed within the first chamber 242, and the second material 316 disposed within the membrane 314. However, alternative embodiments can include a tension member securing mechanism that comprises one or more of these components and/or additional components.

In the embodiment shown, a portion of the elongate member wall 236 extends away from the lengthwise axis 215 of the elongate member 214 and about the entire circumference of the elongate member 214. In the illustrated embodiment, the elongate member body 234 defines a first chamber wall 238 and the flexible member body 334 defines a second chamber wall 335, as described in more detail herein. The first chamber wall 238 and the second chamber wall 335 cooperatively define the first chamber 242 about a portion of the circumference of the elongate member 214, which is sized and configured to receive the first material 222, the cutting element 312, the membrane 314, the second material 316, and a portion of the tension member 220. Thus, the elongate member body 234 and the flexible member body 334 cooperatively define the first chamber 242. However, alternative embodiments can include an elongate member wall that extends about a portion of the circumference of an elongate member and/or an elongate member that cooperatively defines a chamber with a flexible member along the entirety of the circumference of an elongate member. Alternatively, an elongate member can define a recess that defines a first portion of a chamber wall.

In the embodiment illustrated, the elongate member wall 236 defines an opening 320 and a recess 322 that extends around the entire perimeter of the opening 320. The recess 322 is sized and configured to receive a portion of the flexible member 310. Alternatively, a recess can be defined around a portion of the circumference of an opening defined by an elongate member.

The connector 308 is attached to the proximal end 230 of the elongate member 214 and comprises any suitable connector or adapter capable of attaching one or more devices to the elongate member 214. Example connectors or adapters considered suitable to include on an elongate member include threaded connectors, Tuohy Borst adapters, luer lock connectors, conical connectors (e.g., cones, sockets), and any other connector or adapter considered suitable for a particular embodiment.

The flexible member 310 is attached to the elongate member 214 within the recess 322 defined by the elongate member 214 such that the flexible member 310 and the elongate member 214 cooperatively define the first chamber 242. The flexible member 310 has a proximal end 330, a distal end 332, and a body 334 that defines a second chamber wall 335, an outer surface 336, and an inner surface 338. The flexible member 310 is movable between a first position, as shown in FIG. 7, and a second position, as shown in FIG. 8.

The flexible member 310 can be attached to the elongate member 314 using any suitable technique or method of attachment, and skilled artisans will be able to select a suitable technique or method of attachment between a flexible member and an elongate member according to a particular embodiment based on various considerations, including the material(s) that forms a flexible member and/or and elongate member of a medical device. Example techniques and methods of attachment between a flexible member and an elongate member considered suitable include using adhesives, friction fit configurations, snap fit configurations, combinations of those described herein, and any other technique or method considered suitable for a particular embodiment. Alternative to the flexible member 310 being a separate component attached to an elongate member 214, a flexible member can comprise a portion of an elongate member.

The flexible member 310 can be formed of any suitable material and fabricated using any suitable technique or method, and skilled artisans will be able to select a suitable material to form a flexible member and a suitable technique or method to fabricate a flexible member according to a particular embodiment, based on various considerations, including the material(s) that forms an elongate member. Example materials considered suitable to form a flexible member include biocompatible materials, materials that can be made biocompatible, plastics, thin-film plastics, polymers, the materials described herein, and any other material considered suitable for a particular embodiment. Example methods and techniques considered suitable to fabricate a flexible member include extrusion processes, molding processes, injection molding, and any other method or technique considered suitable for a particular embodiment. In the illustrated embodiment, the flexible member 310 is formed of a first material and the elongate member 214 is formed of a second material that is different than the first material. The first material is relatively more flexible than the second material such that the flexible member 310 can be moved from the first position to the second position. Alternatively, a flexible member can be formed of the same material that forms an elongate member.

The cutting element 312 is attached to the inner surface 338 of the flexible member 310 and is disposed within the first chamber 242 cooperatively defined by the elongate member 214 and the flexible member 310. The cutting element 312 has a first end 340, a second end 342, and a body 344 that defines a cutting element passageway 346. The first end 340 of the cutting element 312 is attached to the inner surface 338 of the flexible member 310 and has a first surface area. The second end 342 is disposed within the first chamber 242 and has a second surface area that is less than the first surface area of the first end 340. Thus, the cutting element 312 has a cross-sectional surface area that decreases from the first end 340 to the second end 342. This structural configuration forms the cutting element 312 such that the amount of damage caused to the membrane 314 is increased as the flexible member 310 moves from its first position to its second position relative to a cutting element that does not have a surface area that decreases from the first end to the second end. However, alternative embodiment can include a cutting element that has a cross-sectional surface area that increases, or is continuous, from the first end of the cutting element to the second end of the cutting element. In the illustrated embodiment, the second end 342 of the cutting element 312 is pointed such that it damages the membrane 314 as the flexible member 310 is moved from the first position to the second position. Thus, the cutting element 312 is configured to damage the membrane 314 when the flexible member 310 is moved from the first position to the second position.

In the illustrated embodiment, the cutting element 312 has a right regular square pyramid shape. However, alternative embodiments can include cutting elements that have any suitable size and shape. For example, a cutting element included on a medical device can be configured such that it is pointed, tapered, and/or comprises a needle, a spherical wedge, a triangular prism, an elongate member that has a sharp second end, a blade, and/or an element that has a cutting edge.

The cutting element passageway 346 is disposed between the first end 340 and the second end 342 and is sized and configured to receive a portion of the tension member 220. The cutting element passageway 346 is defined on the cutting element 312 such that it is closer to the second end 342 than it is to the first end 340. Thus, a first distance is disposed between the first end 340 and the cutting element passageway 346 and a second distance is disposed between the second end 342 and the cutting element passageway 346 that is less than the first distance. This configuration provides a mechanism to position a portion of the tension member 220 within a mixed portion of the first material 222 and the second material 316 when the flexible member 310 is in the second position, as described in more detail herein.

In the illustrated embodiment, the cutting element passageway 346 has a first end 348 and a second end 350 and is positioned such that the first end 348 is directed toward the first plug 216 and the second end 350 is directed toward the second plug 218. In the illustrated embodiment, each of the passageway 266 defined by the first plug 216, the passageway 280 defined by the second plug 218, and the cutting element passageway 346 is positioned on a plane. However, alternative embodiments can position a passageway defined by a first plug, a passageway defined by a second plug, and/or a passageway defined by a cutting element on a single plane, or multiple planes.

The cutting element 312 can be formed of any suitable material and fabricated using any suitable technique or method, and skilled artisans will be able to select a suitable material to form a cutting element and a suitable technique or method to fabricate a cutting element according to a particular embodiment, based on various considerations, including the material(s) that forms a membrane included in a medical device of which the cutting element is a component. Example materials considered suitable to form a cutting element include biocompatible materials, materials that can be made biocompatible, metals such as stainless steel, titanium, nickel-titanium alloy (e.g., Nitinol), polymers, Pebax (Pebax is a registered trademark of AtoChimie Corporation of Allee des Vosges, Courbevoie, France), nylon, polyethylene, polyurethane, silicone, the materials described herein, and any other material considered suitable for a particular application. Example methods and techniques considered suitable to fabricate a cutting element include extrusion processes, molding processes, injection molding, and any other method or technique considered suitable for a particular embodiment. For example, the cutting element may optionally be formed as part of a flexible member and/or elongate member. The cutting element can optionally be formed of the same material as the flexible member and/or elongate member and/or have a durometer hardness that is greater than, less than, equal to, or substantially equal to, the flexible member and/or elongate member.

In the illustrated embodiment, the membrane 314 is disposed within the first chamber 242 cooperatively defined by the elongate member 214 and the flexible member 310 between the cutting element 312 and the elongate member 214. The membrane 314 is attached to the elongate member 214 using an adhesive and is movable between a sealed configuration, as shown in FIG. 7, in which the second material 316 is prevented from passing into the first chamber 242 and an unsealed configuration, as shown in FIG. 8. However, alternative embodiments can include a membrane that is attached to an elongate member using any suitable technique or method of attachment, such as those described herein.

The membrane 314 has a membrane wall 354 that defines a second chamber 356 within the first chamber 242 that is sized and configured to receive the second material 316. The membrane 314 separates the second chamber 356 from the first chamber 242 when the flexible member 310 is in the first position. The membrane wall 354 is formed of a material and has a thickness that is configured to be damaged by the cutting element 312 when the flexible member 310 is moved from its first position to its second position. When the membrane 314 has been damaged by the cutting element 312 the second chamber 356 is in fluid communication with the first chamber 242. Alternative embodiments can include a membrane that has a membrane wall that has a scored portion, or that is formed with a first portion that has a first thickness and a second portion that has a second thickness that is less than the first thickness. In these alternative embodiments, the scored portion, or second thickness, can be positioned on the membrane such that the scored portion, or second thickness, will be contacted by the cutting element when the flexible member moves from the first position to the second position and/or such that its shape corresponds to the shape of the cutting element. In the embodiment illustrated, the membrane 314 is entirely disposed within the chamber 242 defined by the elongate member 214 and the flexible member 310. However, alternative embodiments can include a membrane that is partially disposed within a chamber defined by an elongate member and a flexible member.

While the membrane 314 has been illustrated as a separate element attached to the elongate member 214, a membrane can alternatively comprise a portion of the elongate member. In addition, while the membrane 314 has been illustrated as entirely defining the second chamber 356, a membrane can define a first chamber wall and an elongate member can define a second chamber wall that cooperatively defines the second chamber with the first chamber wall. Thus, the elongate member and the membrane can cooperatively define a second chamber. When the elongate member and the membrane cooperatively define a second chamber, the membrane can comprise any suitable structural arrangement, such as a sheet of material that is attached to the elongate member using any suitable method of attachment, such as those described herein (e.g., adhesive, fusing).

The membrane 314 can be formed of any suitable material and fabricated using any suitable technique or method, and skilled artisans will be able to select a suitable material to form a membrane and a suitable technique or method to fabricate a membrane according to a particular embodiment, based on various considerations, including the material(s) that forms a cutting element included in a medical device of which the membrane is a component. Example materials considered suitable to form a membrane include biocompatible materials, materials that can be made biocompatible, silicone, plastics, thin-film plastics, polymers, polyethylene, polypropylene, and any other material considered suitable for a particular embodiment. Example methods and techniques considered suitable to fabricate a membrane include extrusion processes, molding processes, injection molding, and any other method or technique considered suitable for a particular embodiment. In the illustrated embodiment, the cutting element 312 is formed of a first material and the membrane 314 is formed of a second material that is different than the first material. The first material is relatively more rigid than the second material such that the cutting element 312 can damage the membrane 314 as the flexible member 310 is moved to its second position. Alternatively, a membrane can be formed of the same material that forms an elongate member.

In the embodiment illustrated, the first material 222 disposed within the first chamber 242 cooperatively defined by the elongate member 214 and the flexible member 310 is a first part of a liquid hardenable material and the second material 316 disposed within the second chamber 356 is a second part of a liquid hardenable material. In the illustrated embodiment, the first part of the liquid hardenable material comprises an epoxy hardener and the second part of the liquid hardenable material comprises an epoxy resin. The first material 222 is present at a first volume and the second material 316 is present at a second volume that is less than the first volume. However, alternative embodiments can include a first material that is present at a first volume and a second material that is present at a second volume that is greater than, equal to, or substantially equal to, the first volume and/or a first material that is an epoxy hardener and a second material that is an epoxy resin.

While particular materials have been described as disposed within the first chamber 242 defined by the elongate member 214 and the flexible member 310 and within the second chamber 356, the material is disposed within a chamber defined by an elongate member and a flexible member and the material disposed within a chamber defined by a membrane can comprise any suitable material capable of hardening when the first material and the second material are in fluid communication. Skilled artisans will be able to select a suitable material to include in a chamber defined by an elongate member and a flexible member and/or a chamber defined by a membrane according to a particular embodiment based on various considerations, including the material(s) that forms the elongate member, a plug, a tension member, and/or a flexible member included in a medical device of which the material is a component. Example materials considered suitable to include in a chamber defined by an elongate member and a flexible member and/or a chamber defined by a membrane include biocompatible materials, materials that can be made biocompatible, a first part of a liquid hardenable material, a second part of a liquid hardenable material, medical grade materials, hydrophobic materials, non-hydrophobic materials, inert materials, fluids, gels, viscous materials, viscous flowable materials, high viscosity materials, high viscosity fluids, silicone, liquid silicone, liquid silicone rubber, silicone gel, medical grade silicone (e.g., Dow-Corning 360 Medical Fluid), resins, liquid resins, anaerobically curable resins, polyurethane polyacrylate resins, liquid resin hardeners, epoxy resins, uncured epoxy resins, a first part of an epoxy resin, a second part of an epoxy resin, cyanoacrylates, vinyl resins, silicone resins, silicone-acrylate resins, epoxy hardeners, uncured epoxy hardeners, polyepoxides, polyfunctional amines, acids, phenols, alcohols, thiols, sealant materials, and any other material considered suitable for a particular embodiment. The first material 222 is configured such that when it is admixed with the second material 316 the combined material cures in an interval of time (e.g., milliseconds, seconds, minutes) to fix the position of the tension member 220. Optionally, a medical device can include a first material disposed within the chamber cooperatively defined by the elongate member and the flexible member that has a first viscosity and a second material disposed within the chamber defined by the membrane that has a second viscosity that is greater than the first viscosity. Alternatively, the second viscosity can be less than, equal to, or substantially equal to, the first viscosity.

The tension member 220 has a first end 284, a second end 286, and a body 288. The first end 284 is attached to the wall 236 near the distal end 232 of the elongate member 214 and the second end 286 is free of attachment to the elongate member 214. The tension member 220 extends from the first end 284, along a portion of the outer surface of the elongate member 214, through the third passageway 252 and into the elongate member lumen 240, through a portion of the elongate member lumen 240, through the first plug passageway 266, through a first portion of the first chamber 242, through the cutting element passageway 346, through a second portion of the first chamber 242, and through the second plug passageway 280. The tension member 220 is movable between a first position, as shown in FIG. 7, and a second position, as shown in FIG. 8, such that when the tension member 220 is in the first position the elongate member 214 is in the first configuration and when the tension member 220 is in the second position the elongate member 214 is in the second configuration.

While tension member 220 has been illustrated as disposed within a cutting element passageway 346, a medical device can include a tension member that is positioned in any suitable configuration on the medical device. Skilled artisans will be able to select a suitable position for a tension member on a medical device according to a particular embodiment based on various considerations, including the structural arrangement of an elongate member, a chamber, a cutting element, a flexible member, and/or a membrane of a medical device of which the tension member is a component. For example, alternative to being disposed within a passageway defined by a cutting element, a tension member can be disposed between the flexible member and the membrane, attached to the elongate member within the first chamber, or attached to a side of a cutting element and/or membrane.

In use, a force is applied on the tension member 220 that is directed in the proximal direction (e.g., away from the distal end 232 of the elongate member 214) such that the elongate member 214 moves from the first configuration to the second configuration. The second material 316 disposed within the second chamber 356 is separated from the first material 222 when the flexible member 310 is in the first position. Subsequently, a force is applied on the outer surface 336 of the flexible member 310 that is directed toward the elongate member 214 such that the cutting element 312 damages the membrane 314 and the first chamber 222 and the second chamber 356 are in fluid communication with one another. The structural arrangement of the cutting element 312 provides a mechanism for increasing the damage to the membrane 314 (e.g., the size of the opening) as the flexible member 310 moves from the first position to the second position. When the membrane 314 has been damaged, the first material 222 (e.g., the first part of the liquid hardenable material) is in fluid communication with, and reacts with, the second material 316 (e.g., second part of the liquid hardenable material) such that the combined materials harden and fix the tension member 220 in the second position. This provides a mechanism for positioning the elongate member 214 in a desired configuration such that additional treatment can be performed without having to manipulate the position of the tension member 220.

In the illustrated embodiment, the cutting element 312 is not in contact with the membrane 314 when the flexible member 310 is in the first position such that a portion of the cutting element 312 is disposed within the first chamber 242 and the cutting element 312 is in contact with the membrane 314 when the flexible member 310 is in the second position such that the portion of the cutting element 312 is disposed within the membrane chamber 356. Thus, the first material 222 and the second material 316 are separated from one another when the flexible member 310 is in the first position and the first material 222 and the second material 316 are in fluid communication when the flexible member 310 is in the second position. However, alternative embodiments can include a cutting element that is in contact with the membrane when the flexible member is in the first position and/or that does not have a portion disposed within the chamber defined by the membrane when the flexible member is in the second position.

FIG. 9 illustrates another example embodiment of a medical device 410. The medical device 410 is similar to the medical device 210 illustrated in FIGS. 5, 6, 7, and 8 and described above, except as detailed below. The medical device 410 comprises a tension member seal 412, an elongate member 414, a first plug 416, a second plug 418, a tension member 420, a first material 422, a tension member securing mechanism 506, a connector 508, a flexible member 510, a cutting element 512, a membrane 514, and a second material 516 disposed within the membrane 514. The medical device 410 is movable between a first configuration and a second configuration. In the embodiment shown, the tension member seal 412 comprises the first plug 416 disposed within the first passageway 448, the second plug 418 disposed within the second passageway 450, and the material 422 disposed within the chamber 442. In the embodiment shown, the tension member securing mechanism 506 comprises the first material 422 disposed within the chamber 442 defined by the elongate member 414, the flexible member 510 attached to the elongate member 414, the cutting element 512 attached to the flexible member 510, the membrane 514 disposed within the chamber 442, and the second material 516 disposed within the membrane 514.

In the illustrated embodiment, the elongate member 414 includes a separate housing 558 attached to the wall 436. The separate housing 558 defines the chamber 442.

In embodiment shown, the elongate member 414 has a proximal end 430, a distal end 432, and an elongate member body 434 that defines a wall 436, an elongate member lumen 440, a first opening 444, a second opening 446, a first passageway 452, and a second passageway 560. The first passageway 452 extends through the wall 436 and is disposed between the proximal end 430 and the distal end 432 of the elongate member 414. The second passageway 560 extends through the wall 436 and is disposed between the first passageway 452 and the proximal end 430 of the elongate member 414. Each of the first passageway 452 and second passageway 562 is sized and configured to receive a portion of the tension member 420 such that the tension member 420 can be moved between its first and second positions.

The housing 558 has a proximal end 562, a distal end 564, and a chamber wall 438 that defines the chamber 442, a first passageway 448, a second passageway 450, an opening 520, and a recess 522. The chamber 442 is sized and configured to receive a portion of the tension member 420, the first material 422, the cutting element 512, the membrane 514, and the second material 516. The recess 522 extends into the chamber wall 438, around the perimeter of the opening 520, and is sized and configured to receive a portion of the flexible member 510.

The first passageway 448 extends through the chamber wall 438 on the distal end 564 of the housing 558 and provides access between the chamber 442 and an environment exterior to the chamber 442. In the illustrated embodiment, the first passageway 448 provides access to the chamber 442 and the environment exterior to the elongate member lumen 440 and is in communication with the chamber 442 and the environment exterior to the elongate member lumen 440. The second passageway 450 extends through the chamber wall 438 on the proximal end 562 of the housing 558 and provides access between the chamber 442 and an environment exterior to the chamber 442. In the illustrated embodiment, the second passageway 450 provides access to the chamber 442 and the environment exterior to the elongate member lumen 440 and is in communication with the chamber 442 and the environment exterior to the elongate member lumen 440. In the embodiment illustrated, the first passageway 448 and the second passageway 450 are directed toward one another.

The first plug 416 is disposed within the first passageway 448 such that the first end 456 is disposed within the first passageway 448 and the second end 458 is disposed within the chamber 442. The second plug 418 is disposed within the second passageway 450 such that the first end 470 is disposed within the chamber 442 and the second end 472 is disposed flush with the chamber wall 438. Alternative embodiments, however, can include a first plug that extends entirely through the first passageway, a first plug that has a first end disposed in an environment exterior to the elongate member lumen, a first plug that has a first end flush with an outer surface of the chamber wall, a first plug that has a second end disposed within the first passageway, a first plug that has a second end that is flush with an inner surface of the chamber wall, a second plug that extends entirely through the second passageway, a second plug that has a first end disposed flush with an inner surface of the chamber wall, a second plug that has a first end that is disposed within the second passageway, a second plug that has a second end that is disposed in an environment exterior to the elongate member lumen, and/or a second plug that has a second end that is disposed within the second passageway.

The flexible member 510 is partially disposed within the recess 522 and is attached to the housing 558 within the recess 522 as described above with respect to the attachment between the flexible member 310 and elongate member 214, as illustrated in FIGS. 5, 6, 7, and 8.

In the illustrated embodiment, the cutting element 512 is a spherical wedge that has a first end 540 (e.g., spherical lune) attached to the flexible member 510 and a second end 542 disposed within the chamber 442. In addition, the membrane 514 is attached to the chamber wall 438 as described above with respect to the attachment between the membrane 314 and the elongate member 214, as illustrated in FIGS. 5, 6, 7, and 8.

FIG. 10 illustrates another example embodiment of a medical device 610. The medical device 610 is similar to the medical device 210 illustrated in FIGS. 5, 6, 7, and 8 and described above, except as detailed below. The medical device 610 comprises a tension member seal 612, an elongate member 614, a first plug 616, a second plug 618, a tension member 620, a first material 622 disposed within a portion of the elongate member 614, a tension member securing mechanism 706, a connector 708, a flexible member 710, a cutting element 712, a membrane 714, and a second material 716 disposed within the membrane 714. The medical device 610 is movable between a first configuration and a second configuration. In the embodiment shown, the tension member seal 612 comprises the first plug 616 disposed within the first passageway 648, the second plug 618 disposed within the second passageway 650, and the material 622 disposed within the chamber 642. In the embodiment shown, the tension member securing mechanism 706 comprises the first material 622 disposed within the chamber 642 defined by the elongate member 614, the flexible member 710 attached to the elongate member 614, the cutting element 712 attached to the flexible member 710, the membrane 714 disposed within the chamber 642, and the second material 716 disposed within the membrane 714.

In the illustrated embodiment, in addition to defining a first passageway 648, a second passageway 650, and a third passageway 652, the elongate member body 634 defines a fourth passageway 766 and a notch 768.

In the illustrated embodiment, the first passageway 648 extends through the wall 636 between the proximal end 630 and the distal end 632 of the elongate member 614 and provides access between an environment exterior to the elongate member lumen 640 and the chamber 642. In the illustrated embodiment, the first passageway 648 provides access between the chamber 642 and the environment exterior to the elongate member lumen 640 and is in communication with the chamber 642 and the environment exterior to the elongate member lumen 640. The second passageway 650 extends through the wall 636 and provides access between the chamber 642 and an environment exterior to the chamber 642. In the illustrated embodiment, the second passageway 650 provides access between the chamber 642 and the elongate member lumen 640 and is in communication with the chamber 642 and the elongate member lumen 640. The first passageway 648 and the second passageway 650 are directed toward one another.

In the illustrated embodiment, the fourth passageway 766 is disposed between the first passageway 644 and the third passageway 652 and extends through the wall 636 and provides access between an environment exterior to the elongate member lumen 640 and the elongate member lumen 640. In the illustrated embodiment, the fourth passageway 766 provides access between the elongate member lumen 640 and the environment exterior to the elongate member lumen 640 and is in communication with the elongate member lumen 640 and the environment exterior to the elongate member lumen 640.

The notch 768 is defined between the first passageway 648 and the fourth passageway 766 such that a portion of the tension member 620 can be positioned within the notch 768, as described in more detail herein. In the illustrated embodiment, the notch 768 is sized and configured such that a first end of the first passageway 648 and a first end of the fourth passageway 766 can be positioned within the notch 768. Alternatively, an elongate member can omit the inclusion of a notch and can define a first passageway and a second passageway that are each in communication with an environment exterior to the elongate member lumen.

In the illustrated embodiment, the first plug 616 is partially disposed in the chamber 642, the first passageway 648, the notch 768, and the fourth passageway 766. The first end 656 of the first plug 616 is disposed flush with the inner wall of the wall 636 and the second end 658 of the first plug 616 is disposed within the chamber 642. Alternatively, a first plug can have a first end that is disposed within an elongate member lumen, a first plug can have a first end that is disposed within the first passageway, a first plug can have a second end that is flush with the inner wall of a chamber wall, and/or a first plug can have a second end that is disposed within the first passageway.

In the illustrated embodiment, the second plug first opening 676 is in communication with the chamber 642 and the second plug second opening 678 is in communication with an environment exterior to the chamber 642. In the illustrated embodiment, each of the second plug second opening 678 and second plug passageway 680 is in communication with the elongate member lumen 640. While the second passageway 650 and the second plug second end 678 are illustrated as being in communication with the elongate member lumen 640, the second passageway and second plug second end of a medical device can alternatively be in communication with an environment exterior to the elongate member lumen.

In the illustrated embodiment, the cutting element 712 comprises a triangular prism that has a first end 740 attached to the flexible member 710.

The tension member 620 extends from the first end 684, along a portion of the outer surface of the elongate member 614, through the third passageway 652 and into the elongate member lumen 640, through a portion of the elongate member lumen 640, through the first plug passageway 666, through a first portion of the chamber 642, through the passageway 746 defined by the cutting element 712, through a second portion of the chamber 642, through the second plug passageway 680, through the elongate member lumen 640 and the elongate member proximal end 630 to an environment exterior to the elongate member lumen 640.

In the illustrated embodiment, the structural configuration between the first passageway 648, the first plug 616, the tension member 620, the fourth passageway 766, and the notch 768 provide a structural arrangement that allows a user to cut the tension member 620 after treatment has been completed. For example, when the tension member 620 is moved from the first position to the second position and a desired radius of curvature has been formed in the elongate member 614, a user can fix the elongate member 614 in the desired curved configuration by moving the flexible member 710 from its first position to its second position. Subsequently, when it is desired to move the elongate member 614 from its second configuration to its first configuration, a user can cut the tension member 620 within the notch 768.

FIG. 11 illustrates another example embodiment of a medical device 810. The medical device 810 is similar to the medical device 610 illustrated in FIG. 10 and described above, except as detailed below. The medical device 810 comprises a tension member seal 812, an elongate member 814, a first plug 816, a second plug 818, a tension member 820, a first material 822 disposed within a portion of the elongate member 814, a tension member securing mechanism 906, a connector 908, a flexible member 910, a cutting element 912, a membrane 914, and a second material 916 disposed within the membrane 914. The medical device 810 is movable between a first configuration and a second configuration. In the embodiment shown, the tension member seal 812 comprises the first plug 816 disposed within the first passageway 848, the second plug 818 disposed within the second passageway 850, and the material 822 disposed within the chamber 842. In the embodiment shown, the tension member securing mechanism 906 comprises the first material 822 disposed within the chamber 842 defined by the elongate member 814, the flexible member 910 attached to the elongate member 814, the cutting element 912 attached to the elongate member 814, the membrane 914 attached to the flexible member 910, and the second material 916 disposed within the membrane 914.

In the illustrated embodiment, the first plug 816 is partially disposed within the first passageway 848, the cutting element 912 is attached to the elongate member 814 and the membrane 914 is attached to the flexible member 910.

The first end 856 of the first plug 816 is positioned such that it does not extend into the notch 968. However, alternative embodiments can include a first plug that has a first end that is disposed within a notch defined by an elongate member, a first plug that has a first end disposed flush with the chamber wall, or a first plug that has a first end disposed within the first passageway. Thus, in the embodiment shown, only the tension member 820 is disposed within the notch 968. This provides a mechanism for moving the elongate member 814 from the second configuration to the first configuration by cutting only the tension member 820.

In the illustrated embodiment, the cutting element 912 is similar to the cutting element 512 described above with respect to FIG. 9 and is attached to the elongate member 814. The membrane 914 is attached to the flexible member 910 such that when the flexible member 910 is moved from its first position to its second position the membrane 914 will contact the cutting element 912 and become damaged.

FIG. 12 illustrates another example embodiment of a medical device 1010. The medical device 1010 is similar to the medical device 610 illustrated in FIG. 10 and described above, except as detailed below. The medical device 1010 comprises a tension member seal 1012, an elongate member 1014, a first plug 1016, a second plug 1018, a tension member 1020, a first material 1022 disposed within a portion of the elongate member 1014, a tension member securing mechanism 1106, a connector (not shown), a flexible member 1110, a cutting element 1112, a membrane 1114, and a second material 1116 disposed within the membrane 1114. The medical device 1010 is movable between a first configuration and a second configuration. In the embodiment shown, the tension member seal 1012 comprises the first plug 1016 disposed within the first passageway 1048, the second plug 1018 disposed within the second passageway 1050, and the material 1022 disposed within the chamber 1042. In the embodiment shown, the tension member securing mechanism 1106 comprises the first material 1022 disposed within the chamber 1042 defined by the elongate member 1014, the flexible member 1110 attached to the elongate member 1014, the cutting element 1112 attached to the flexible member 1110, the membrane 1114 disposed within the chamber 1042, and the second material 1116 disposed within the membrane 1114.

In the illustrated embodiment, the elongate member 1014 omits the inclusion of a recess and a notch and the medical device 1010 includes an actuator 1170 and an o-ring 1172.

In the illustrated embodiment, the flexible member 1110 is attached to the outer surface of the elongate member 1014 and defines an opening 1174 that is sized and configured to receive a portion of the actuator 1170, as described in more detail herein. The opening 1174 is positioned on the flexible member 1110 such that it is aligned with the membrane 1114 (e.g., the opening 1174 is disposed on an axis with the membrane 1114). Alternatively, a medical device can omit the inclusion of a flexible member and the elongate member can define an opening (e.g., opening 1174) that is sized and configured to receive a portion of an actuator.

The actuator 1170 is disposed within the opening 1174 defined by the flexible member 1130 and is movable within the opening 1174. In the illustrated embodiment, the actuator 1170 comprises a depressible member that can be advanced into the chamber 1042 such that is moves between first and second positions. However, alternative embodiments can include an actuator that is attached to a flexible member and/or elongate member using any suitable technique or method of attachment, such as fusing the actuator to the flexible member and/or elongate member, using adhesive, or forming the actuator as part of the flexible member (e.g., the actuator and the flexible member are integrated components) and/or elongate member.

The actuator 1170 comprises a proximal end 1176, a distal end 1178, a main body 1180, a first projection 1182, and second projection 1184. The main body 1180 defines a top surface 1186 and a passageway 1188. In the illustrated embodiment, the top surface 1186 is disposed in an environment exterior to the chamber 1042. However, alternative embodiments can include an actuator that defines a top surface that is coplanar with the outer surface of a flexible member and/or elongate member. The cutting element 1112 is attached to the main body 1180 of the actuator 1170 and is positioned such that it can damage the membrane 1114 when actuator 1170 is moved from its first position to its second position. The passageway 1188 extends from a first opening defined on the proximal end 1176 of the actuator 1170 to a second opening defined on the distal end 1178 of the actuator 1170. The passageway is sized and configured to receive a portion of the tension member 1020.

Each of the first projection 1184 and the second projection 1186 extends from the main body 1180 and toward the elongate member body 1034. Each of the first projection 1184 and the second projection 1186 comprises a flexible member that biases the actuator 1170 toward its first position. While first and second projections 1184, 1186 have been illustrated, a medical device can include any suitable number of projections, such as one, at least one, two, a plurality, three, four, and any other number of projections considered suitable for a particular embodiment.

While an actuator 1170 that comprises a depressible member has been illustrated, a medical device can include any suitable actuator capable of moving a flexible member between its first and second positions. Skilled artisans will be able to select a suitable actuator to include in a medical device according to a particular embodiment based on various considerations, including the structural arrangement of an elongate member. Example actuators considered suitable to include in a medical device include depressible members, rotatable members, slidable members, linear actuators, pivotable actuators, levers, and any other actuator considered suitable for a particular embodiment.

The actuator 1170 can be formed of any suitable material and can be fabricated using any suitable method or technique. Skilled artisans will be able to select a suitable material to form an actuator and a suitable method or technique to fabricate an actuator according to a particular embodiment based on various considerations, including the desired flexibility of the actuator. Example materials considered suitable to form an actuator include biocompatible materials, materials that can be made biocompatible, metals such as stainless steel, titanium, nickel-titanium alloy (e.g., Nitinol), polymers, Pebax (Pebax is a registered trademark of AtoChimie Corporation of Allee des Vosges, Courbevoie, France), nylon, polyethylene, polyurethane, silicone, and any other material considered suitable for a particular application. Example methods and techniques considered suitable to fabricate an actuator include extrusion processes, molding processes, injection molding, and any other method or technique considered suitable for a particular embodiment.

The o-ring 1172 is disposed between the flexible member 1110 and the first and second projections 1182, 1184 of the actuator 1170. The o-ring 1172 comprises a deformable member that defines an aperture 1190 through which the main body 1180 of the actuator 1170 is disposed. The o-ring 1172 provides a mechanism for preventing the first material 1022 from exiting the chamber 1042 between the main body 1180 and the flexible member 1110. The aperture 1190 has an inside diameter that is equal to, or less than, the outer diameter of the main body 1180 such that releasable friction fit attachment between the o-ring 1172 and the main body 1180 can be accomplished.

The o-ring 1172 can comprise any suitable structure, can be formed of any suitable material, and can define any suitable inside diameter, and skilled artisans will be able to select a suitable structure for an o-ring, and a suitable material for an o-ring according to a particular embodiment based on various considerations, such as the outer diameter of the main body of an actuator. It is considered advantageous to form an o-ring of a flexible, or substantially flexible, material relative to the material that forms an actuator such that a sealing engagement between the actuator and the o-ring and between the o-ring and the flexible member can be achieved.

In the illustrated embodiment, the tension member 1020 extends from the first end (not shown), along a portion of the outer surface of the elongate member 1014, through the third passageway (not shown) and into the elongate member lumen 1040, through a portion of the elongate member lumen 1040, through the first plug passageway 1066, through a first portion of the chamber 1042, through the passageway 1188 defined by the main body 1180 of the actuator 1170, through a second portion of the chamber 1042, through the second plug passageway 1080, and through the elongate member lumen 1040 to an environment exterior to the elongate member lumen 1040.

FIG. 13 illustrates another example embodiment of a medical device 1210. The medical device 1210 is similar to the medical device 1010 illustrated in FIG. 12 and described above, except as detailed below. The medical device 1210 comprises a tension member seal 1212, an elongate member 1214, a first plug 1216, a second plug 1218, a tension member 1220, a first material 1222 disposed within a portion of the elongate member 1214, a tension member securing mechanism 1306, a connector (not shown), a flexible member 1310, a cutting element 1312, a membrane 1314, a second material 1316 disposed within the membrane 1314, an actuator 1370, and an o-ring 1372. The medical device 1210 is movable between a first configuration and a second configuration. In the embodiment shown, the tension member seal 1212 comprises the first plug 1216 disposed within the first passageway 1248, the second plug 1218 disposed within the second passageway 1250, and the material 1222 disposed within the chamber 1242. In the embodiment shown, the tension member securing mechanism 1306 comprises the first material 1222 disposed within the chamber 1242 defined by the elongate member 1214, the flexible member 1310 attached to the elongate member 1214, the cutting element 1312 attached to the flexible member 1310, the membrane 1314 disposed within the chamber 1242, and the second material 1316 disposed within the membrane 1314.

In the illustrated embodiment, the medical device 1210 includes a first spring 1392 and a second spring 1394. In addition, the first projection 1382 extends away from the main body 1380 and toward the distal end (not shown) of the elongate member 1214 and the second projection 1384 extends away from the main body 1380 and toward the proximal end (not shown) of the elongate member 1214.

The first spring 1392 is disposed between the first projection 1382 and the elongate member body 1234 and the second spring 1394 is disposed between the second projection 1384 and the elongate member body 1234. Each of the first spring 1392 and second spring 1394 has an expanded configuration, as shown in FIG. 13, when the actuator 1370 is the first position and a compressed configuration when the actuator 1370 is in the second position. Each of the first spring 1392 and second spring 1394 is configured to bias the actuator 1370 to the first position. In the illustrated embodiment, each of the first spring 1392 and second spring 1394 is a compression spring, which exerts a force resisting compression proportional to the distance the spring has been compressed.

While each of the first spring 1392 and second spring 1394 has been described as a particular type of spring, any suitable spring, formed of any suitable material, and having any suitable compressed and/or uncompressed lengths is considered suitable for use in a medical device. Skilled artisans will be able to select a suitable spring, material to form a spring, and suitable compressed and/or uncompressed lengths for a spring according to a particular embodiment based on various considerations, including the amount of force required to move an actuator between its first and second configurations.

Methods of treatment are described herein. While the methods described herein are shown and described as a series of acts, it is to be understood and appreciated that the methods are not limited by the order of acts described and illustrated, as some acts may in accordance with these methods, be omitted, be repeated, or occur in different orders and/or concurrently with other acts described herein. The methods include methods of treatment using a medical device. While some steps, optional steps, and/or alternative steps are exemplified by performing treatment within a bodily passage, the methods, steps, optional steps, and/or alternative steps described herein can also be used to perform any other suitable treatment. Skilled artisans will be able to select a suitable treatment to perform according to the methods, steps, optional steps, and/or alternative steps described herein based on various considerations, such as the condition intended to be treated.

Figure 14:
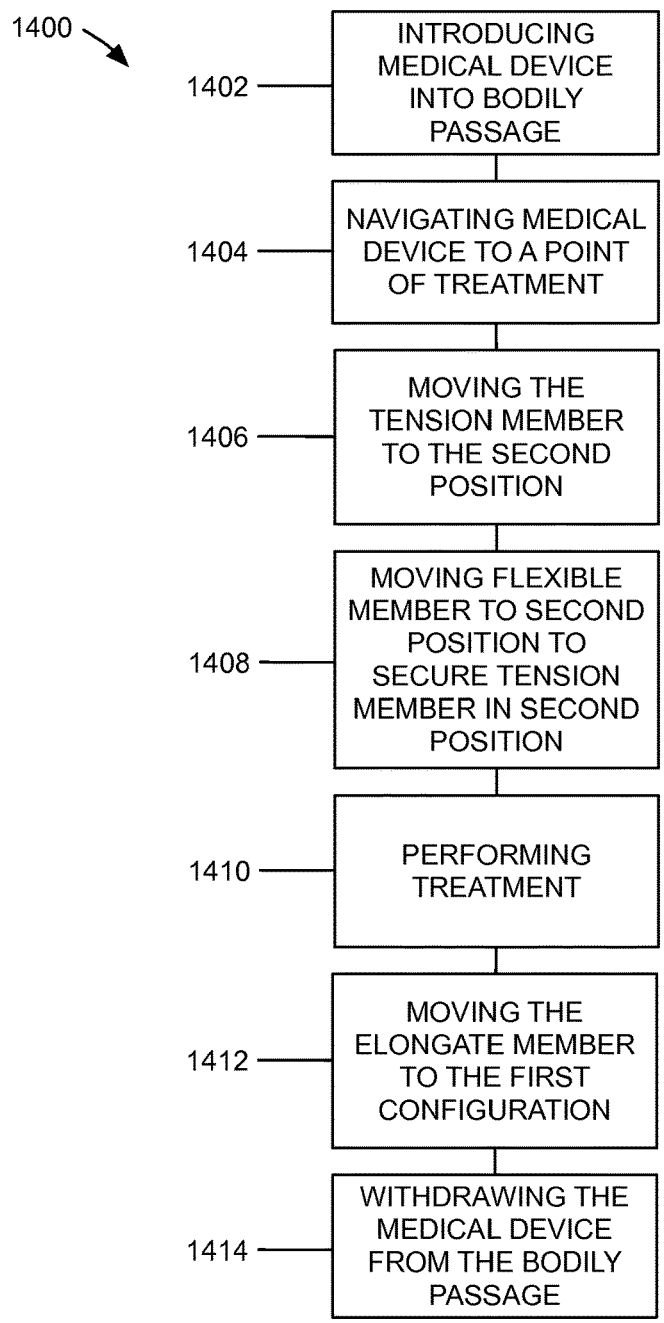
FIG. 14 is a schematic illustration of an example method of treatment.

FIG. 14 is a schematic illustration of an example method of treatment 1400 using a medical device.

A step 1402 comprises introducing a medical device having a proximal end and a distal end into a bodily passage such that the distal end of the medical device is disposed within the bodily passage. Another step 1404 comprises navigating the distal end of the medical device to a point of treatment within the bodily passage. Another step 1406 comprises moving the tension member from the first position to the second position such that the elongate member moves from the first configuration to the second configuration. Another step 1408 comprises moving the flexible member from the first position to the second position such that the membrane is damaged and the first material and the second material are in fluid communication with one another. Another step 1410 comprises performing treatment. Another step 1412 comprises moving the elongate member from the second configuration to the first configuration. Another step 1414 comprises withdrawing the medical device from the bodily passage.

Step 1402 can be accomplished by applying a distally-directed force (e.g., toward the bodily passage) on any suitable portion of a medical device (e.g., elongate member) such that the distal end of the medical device is passed into the bodily passage. Step 1402 can be accomplished using any suitable medical device, and skilled artisans will be able to select a suitable medical device to use in a method of treatment according to a particular embodiment based on various considerations, including the type of treatment being performed. Example medical devices considered suitable to use in a method of treatment include the medical devices described herein, such as medical device 10, medical device 110, medical device 210, medical device 410, medical device 610, medical device 810, medical device 1010, medical device 1210, medical device 1510, medical device 1710, variations thereof, and any other medical device considered suitable for a particular method of treatment. An example medical device that can be used to accomplish the methods, steps, alternative steps, and/or optional steps described herein is illustrated and described with respect to FIGS. 5, 6, 7, and 8, and comprises a tension member seal 212, an elongate member 214, a first plug 216, a second plug 218, a tension member 220, a first material 222 disposed within a portion of the elongate member 214, a tension member securing mechanism 306, a connector 308, a flexible member 310, a cutting element 312, a membrane 314, and a second material 316 disposed within the membrane 314. The medical device 210 is movable between a straight configuration and a curved configuration.

Step 1402 can be accomplished by introducing a medical device into any suitable bodily passage. Skilled artisans will be able to select a suitable bodily passage to introduce a medical device according to a particular embodiment based on various considerations, including the treatment intended to be performed. Example bodily passages considered suitable to introduce a medical device include a portion of the urinary tract, a bodily passage used to perform biliary drainage, a bodily passage used to perform bladder drainage, abscesses, and any other bodily passage considered suitable for a particular embodiment.

Step 1404 can be accomplished by applying a distally-directed force (e.g., toward point of treatment) on any suitable portion of the medical device (e.g., elongate member) until the distal end of the elongate member is disposed at a point of treatment within the bodily passage. Alternatively, step 1404 can be completed such that the distal end of the medical device is disposed near, proximal to, distal to, or adjacent a point of treatment.

Step 1406 can be accomplished by applying a proximally-directed force (e.g., away from the bodily passage) on the tension member until the elongate member moves from its first configuration to its second configuration.

Depending on the medical device used to complete the method of treatment 1400, step 1408 can be accomplished as described below. If medical device 210, medical device 410, medical device 610, medical device 810, medical device 1010, medical device 1210, or medical device 1710 is being used to complete method of treatment 1400, step 1408 can be accomplished by applying a force on the outer surface of the flexible member, or actuator, that is directed toward the elongate member lumen. Alternatively, in embodiments that omit the inclusion of a flexible member (e.g., medical device 10, medical device 110, medical device 1510), step 1408 comprises locking the tension member in the second position and can be accomplished by tying a knot in the tension member, attaching a locking mechanism to the tension member, or by fixing the position of an actuator in the desired second position.

Step 1410 can be accomplished using any suitable device and using any suitable technique and will depend on the treatment intended to be performed. For example, treatment can be performed using a suction catheter such that suction can be performed within the bodily passage. An optional step comprises introducing a suction catheter into the elongate member lumen of a medical device. Another optional step comprises advancing the suction catheter into the bodily passage. Another optional step comprises activating the suction catheter such that suction is performed on the bodily passage. Another optional step comprises deactivating the suction catheter. Another optional step comprises withdrawing the suction catheter from the bodily passage. Another optional step comprises withdrawing the suction catheter from the elongate member lumen. Alternatively, an optional step comprises attaching a suction catheter to the connector (e.g., 308) of a medical device. Another optional step comprises activating the suction catheter such that suction is performed on the bodily passage. Another optional step comprises deactivating the suction catheter. Another optional step comprises removing the suction catheter from the elongate member lumen.

Depending on the medical device used to complete the method of treatment 1400, step 1412 can be accomplished as described below. If medical device 210, medical device 410, medical device 610, medical device 810, medical device 1010, medical device 1210, or medical device 1710 is being used to complete method of treatment 1400, step 1412 can be accomplished by cutting the tension member at a location proximal to the first end of the tension member (e.g., within notch defined by elongate member, along the length of the elongate member, at a location between the first end of the tension member and distal to the first plug, along the length of the first plug). Alternatively, in embodiments that omit the inclusion of a flexible member (e.g., medical device 10, medical device 110, medical device 1510), step 1412 can be accomplished by unlocking the tension member such that it moves from the second position to the first position. This can be accomplished by cutting the tension member such that it is free to move to the first position, by removing the knot in the tension member, detaching the locking mechanism from the tension member, or by releasing the position of an actuator such that it moves to the first position.

Step 1414 can be accomplished by applying a proximally-directed force (e.g., away the bodily passage) on any suitable portion of a medical device (e.g., elongate member) such that the distal end of the medical device is withdrawn from the bodily passage.

FIGS. 15 and 16 illustrate another example embodiment of a medical device 1510. The medical device 1510 is similar to the medical device 10 illustrated in FIGS. 1, 2, and 3 and described above, except as detailed below. The medical device 1510 comprises a tension member seal 1512, an elongate member 1514, a first plug 1516, a second plug 1518, a tension member 1520, and a material 1522 disposed within a portion of the elongate member 1514. The medical device 1510 is movable between a first configuration and a second configuration. In the embodiment shown, the tension member seal 1512 comprises the first plug 1516 disposed within the first passageway 1548, the second plug 1518 disposed within the second passageway 1550, and the material 1522 disposed within the chamber 1542.

In the illustrated embodiment, the elongate member 1514 comprises an elongate member first portion 1610, an elongate member second portion 1612, and a cap 1614. The elongate member first portion 1610 is similar to the elongate member 14 illustrated in FIGS. 1, 2, and 3 and described above, except that the elongate member first portion 1610 does not define the third passageway (e.g., third passageway 52) the elongate member second portion 1612 defines the third passageway 1552. In addition, the elongate member first portion 1610 defines threads 1616. Thus, the elongate member first portion 1610 has a lengthwise axis 1515, a proximal end 1530, a distal end 1532, and an elongate member first portion body 1534 that defines a wall 1536, an elongate member first portion lumen 1540, a chamber 1542, a first opening 1544, a second opening 1546, a first passageway 1548, and a second passageway 1550.

In the illustrated embodiment, the distal end 1532 of the elongate member first portion 1610 is tapered. The threads 1616 are disposed between the proximal end 1530 and the distal end 1532 of the elongate member first portion 1610 and have a helical configuration that is sized and configured to interact with the helical configuration defined by threads 1646 defined by the cap 1614, as described herein. While the threads 1616 have been illustrated as defined on an outer surface of the elongate member first portion 1610, the threads defined by an elongate member portion can alternatively be defined on the inner surface of the elongate member portion. The threads 1616 provide a mechanism to releasably attach the cap 1614 to the elongate member first portion 1610. Alternative embodiments can include threads that extend from the distal end of an elongate member first portion toward the proximal end of the elongate member first portion.

The elongate member second portion 1612 has a proximal end 1618, a distal end 1620, and an elongate member second portion body 1622 that defines a wall 1624, an elongate member second portion lumen 1626, a first opening 1628, a second opening 1630, a passageway 1552, and a plurality of pores 1632. The proximal end 1618 of the elongate member second portion 1612 is flared and sized and configured to be received between the elongate member first portion 1610 and the cap 1614. The elongate member second portion lumen 1626 extends from the first opening 1628 defined on the proximal end 1618 to the second opening 1630 defined on the distal end 1620. The passageway 1552 extends through the wall 1624 and is disposed between the proximal end 1618 and the distal end 1620 of the elongate member second portion 1612. The passageway 1552 is sized and configured to receive a portion of the tension member 1520. Each pore of the plurality of pores 1632 extends through the wall 1624 and is disposed between the passageway 1552 and the distal end 1620 of the elongate member second portion 1612. Each pore of the plurality of pores 1632 is sized and configured to allow a fluid to pass between an environment exterior to the elongate member second portion lumen 1626 and the elongate member second portion lumen 1626. For example, each pore of the plurality of pores 1632 can be used to perform a procedure such as suction and/or irrigation procedures.

While a plurality of pores 1632 have been illustrated, an elongate member can define any suitable number of pores positioned at any suitable location on an elongate member, and skilled artisans will be able to select a suitable number of pores to define on an elongate member of a medical device and a suitable location for each pore according to a particular embodiment based on various considerations, including the treatment intended to be performed. Example number of pores considered suitable to define on an elongate member of a medical device include one, at least one, two, a plurality, three, four, five, six, and any other number considered suitable for a particular embodiment. Example locations for a pore, or a plurality of pores, include between the proximal end and the distal end of an elongate member, between a passageway and the distal end of an elongate member, and any other location considered suitable for a particular embodiment.

In the illustrated embodiment, the cap 1614 is releasably attached to the elongate member first portion 1610. The cap 1614 comprises a proximal end 1634, a distal end 1636, and a body 1638 that defines a first opening 1640, a second opening 1642, a lumen 1644, and threads 1646. The first opening 1640 is defined on the proximal end 1634 and the second opening 1642 is defined on the distal end 1636. The lumen 1644 extends from the first opening 1640 to the second opening 1642.

The lumen 1644 has a first inside diameter 1643 and a second inside diameter 1645. The first inside diameter 1643 is disposed along a proximal portion of the lumen 1644 that extends from the proximal end 1634 of the cap 1614 toward the distal end 1636 of the cap 1614. The second inside diameter 1645 is less than the first inside diameter 1643 and is disposed along a distal portion of the lumen 1644 that extends from the distal end 1636 toward the proximal end 1641. The first inside diameter 1643 tapers to the second inside diameter 1645 along a tapered portion 1648 of the inner surface of the cap 1614 defined between the proximal portion and the distal portion of the cap 1614. Thus, the tapered portion 1648 of the cap 1614 is disposed between the proximal end 1634 and the distal end 1636 of the cap 1614. In the illustrated embodiment, the tapered portion 1648 of the lumen 1644 corresponds to the tapered distal end 1532 of the elongate member first portion 1612 and the flared proximal end 1618 of the elongate member second portion 1612. However, alternative embodiments can include a cap that has a first inside diameter that tapers to a second inside diameter along a portion, or the entirety, of the length of the cap (e.g., along a proximal portion of the cap that extends from the proximal end toward the distal end, along a distal portion of the cap that extends from the distal end toward the proximal end).

Threads 1646 are disposed between the proximal end 1634 and the distal end 1636 of the cap 1614 within lumen 1644 and have a helical configuration that is sized and configured to interact with the helical configuration defined by threads 1616 defined by the elongate member first portion 1610. Threads 1646 provide a mechanism to releasably attach the cap 1614 to the elongate member first portion 1610. While the threads 1646 have been illustrated as defined on an inner surface of the cap 1614, the threads defined by a cap can alternatively be defined on the outer surface of the cap. Alternative embodiments can include threads that extend from the proximal end of a cap toward the distal end of the cap.

An example method of assembling the medical device 1510 comprises passing the distal end 1620 of the elongate member second portion 1612 through the lumen 1644 defined by the cap 1614 such that the flared proximal end 1618 contacts the inner wall of the cap 1614. Subsequently, the cap 1614 can be advanced toward the elongate member first portion 1610 such that the cap 1614 contacts the elongate member first portion 1610. Torque is then applied to the cap 1614 and/or the elongate member first portion 1610 (e.g., in a clockwise direction about the lengthwise axis of the elongate member first portion 1610 and/or cap 1614, in a counterclockwise direction about the lengthwise axis of the elongate member first portion 1610 and/or cap 1614) until a sealed, or substantially sealed, engagement between the elongate member first portion 1610, elongate member second portion 1612, and/or the cap 1614 is accomplished. In the assembled configuration, the lumen 1540 of the elongate member first portion 1610 and the lumen 1626 of the elongate member second portion 1612 are in communication with one another and are coaxial. However, alternative embodiments can include an assembled medical device that includes an elongate member first portion that is not coaxial with an elongate member second portion.

In the embodiment illustrated, the tension member 1520 extends from the first end 1584, along a portion of the outer surface of the elongate member second portion 1612, through the passageway 1552 and into the elongate member lumen 1626 defined by the elongate member second portion 1612, through a portion of the lumen 1626, through a portion of the lumen 1540 defined by the elongate member first portion 1610, through the first plug passageway 1566, through the chamber 1542, and through the second plug passageway 1580. The tension member 1520 is movable between a first position and a second position such that when the tension member 1520 is in the first position the elongate member 1514 is in the first configuration, as shown in FIG. 15, and when the tension member 1520 is in the second position the elongate member 1514 is in the second configuration, as shown in FIG. 16.

In the illustrated embodiment, when the elongate member 1714 is in the first configuration, the passageway 1552 defined by the elongate member second portion 1612 is disposed on a first plane that contains the lengthwise axis of the elongate member second portion 1612 and the attachment location of the first end 1584 of the tension member 1520 is disposed on a second plane that contains the lengthwise axis of the elongate member second portion 1612. In the illustrated embodiment, the first plane is disposed at a 180 degree angle to the second plane (e.g., the first plane is coplanar with the second plane) such that the passageway 1552 is disposed on a first side of the wall 1624 and the attachment location is disposed on an opposably facing second side of the wall 1624. However, alternative embodiments can define any suitable angle between a first plane and a second plane depending on the desired curvature intended to be imparted on an elongate member, such as angles that are equal to, substantially equal to, or about, 180 degrees, 90, degrees, 45 degrees, and any other angle considered suitable for a particular embodiment.

While an interlocking structure has been illustrated between the elongate member first portion 1610 and the cap 1614 to secure the elongate member second portion 1612 to the elongate member first portion 1610, any suitable locking structure can be included on an elongate member first portion, elongate member second portion, and/or a cap to provide releasable attachment between the elongate member first portion and the elongate member second portion. For example, a cap can be omitted and an elongate member first portion can be directly attached to the elongate member second portion. Skilled artisans will be able to select a suitable locking structure to include on an elongate member first portion, elongate member second portion, and/or cap according to a particular embodiment based on various considerations, including the material(s) that forms the elongate member first portion, elongate member second portion, and/or the cap. Example locking structures considered suitable to include on an elongate member first portion, elongate member second portion, and/or a cap include interlocking structures, structures that provide a friction fit between the elongate member first portion, elongate member second portion, and/or the cap, morse taper configurations, threaded connections, structures that provide a snap fit between the elongate member first portion, elongate member second portion, and/or the cap, mechanical fasteners, and any other structure considered suitable for a particular embodiment. Alternatively, an elongate member first portion can be attached to an elongate member second portion and/or a cap by fusing one or more of the elements to each other, or using any other technique or method of attachment, such as adhesives.

Figure 17:
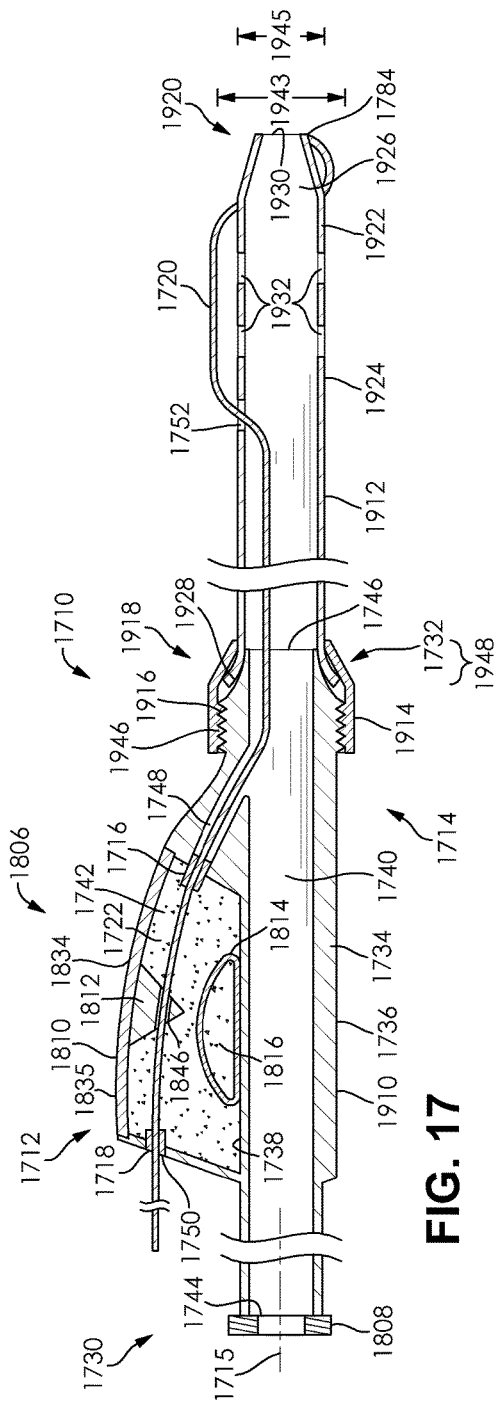
FIG. 17 is a partially broken away sectional view of another example embodiment of a medical device taken along the lengthwise axis of the elongate member. The medical device includes a tension member seal and securing mechanism and is shown in a first configuration.
Figure 18:
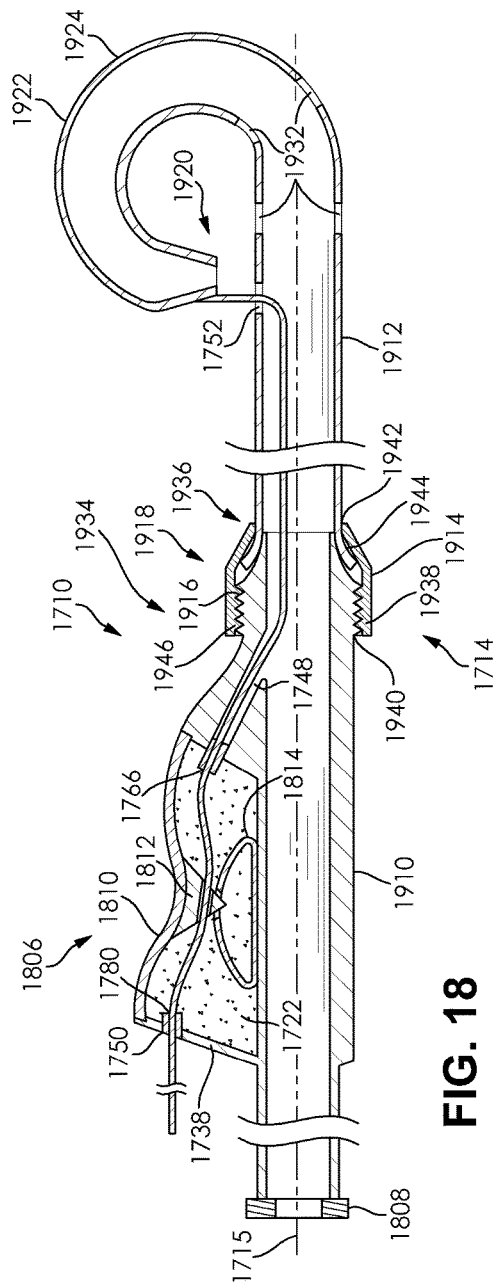
FIG. 18 is a partially broken away sectional view of the medical device illustrated in FIG. 17 taken along the lengthwise axis of the elongate member. The medical device is shown in a second configuration.

FIGS. 17 and 18 illustrate another example embodiment of a medical device 1710. The medical device 1710 is similar to the medical device 210 illustrated in FIGS. 5, 6, 7, and 8 and described above, except as detailed below. The medical device 1710 comprises a tension member seal 1712, an elongate member 1714, a first plug 1716, a second plug 1718, a tension member 1720, a first material 1722, a tension member securing mechanism 1806, a connector 1808, a flexible member 1810, a cutting element 1812, a membrane 1814, and a second material 1816 disposed within the membrane 1814. The medical device 1710 is movable between a first configuration and a second configuration. In the embodiment shown, the tension member seal 1712 comprises the first plug 1716 disposed within the first passageway 1748, the second plug 1718 disposed within the second passageway 1750, and the material 1722 disposed within the chamber 1742. In the embodiment shown, the tension member securing mechanism 1806 comprises the first material 1722 disposed within the chamber 1742 defined by the elongate member 1714, the flexible member 1810 attached to the elongate member 1714, the cutting element 1812 attached to the flexible member 1810, the membrane 1814 disposed within the chamber 1742, and the second material 1816 disposed within the membrane 1814.

In the illustrated embodiment, the elongate member 1714 comprises an elongate member first portion 1910, an elongate member second portion 1912, and a cap 1914. The elongate member first portion 1910 is similar to the elongate member 214 illustrated in FIGS. 5, 6, 7, and 8 and described above, except that the elongate member first portion 1910 does not define the third passageway (e.g., third passageway 252) the elongate member second portion 1912 defines the third passageway 1752. In addition, the elongate member first portion 1910 defines threads 1916. Thus, the elongate member first portion 1910 has a lengthwise axis 1715, a proximal end 1730, a distal end 1732, and an elongate member first portion body 1734 that defines a wall 1736, an elongate member first portion lumen 1740, a first opening 1744, a second opening 1746, a first passageway 1748, and a second passageway 1750.

In the illustrated embodiment, the elongate member body 1734 defines a first chamber wall 1738 and the flexible member body 1834 defines a second chamber wall 1835. The first chamber wall 1738 and the second chamber wall 1835 cooperatively define the first chamber 1742.

In the illustrated embodiment, the distal end 1732 of the elongate member first portion 1910 is tapered. The threads 1916 are disposed between the proximal end 1730 and the distal end 1732 of the elongate member first portion 1910 and have a helical configuration that is sized and configured to interact with the helical configuration defined by threads 1946 defined by the cap 1914, as described herein. While the threads 1916 have been illustrated as defined on an outer surface of the elongate member first portion 1910, the threads defined by an elongate member portion can alternatively be defined on the inner surface of the elongate member portion. The threads 1916 provide a mechanism to releasably attach the cap 1914 to the elongate member first portion 1910. Alternative embodiments can include threads that extend from the distal end of an elongate member first portion toward the proximal end of the elongate member first portion.

The elongate member second portion 1912 has a proximal end 1918, a distal end 1920, and an elongate member second portion body 1922 that defines a wall 1924, an elongate member second portion lumen 1926, a first opening 1928, a second opening 1930, a passageway 1752, and a plurality of pores 1932. The proximal end 1918 of the elongate member second portion 1912 is flared and sized and configured to be received between the elongate member first portion 1910 and the cap 1914. The elongate member second portion lumen 1926 extends from the first opening 1928 defined on the proximal end 1918 to the second opening 1930 defined on the distal end 1920. The passageway 1752 extends through the wall 1924 and is disposed between the proximal end 1918 and the distal end 1920 of the elongate member second portion 1912. The passageway 1752 is sized and configured to receive a portion of the tension member 1720. Each pore of the plurality of pores 1932 extends through the wall 1924 and is disposed between the passageway 1752 and the distal end 1920 of the elongate member second portion 1912. Each pore of the plurality of pores 1932 is sized and configured to allow a fluid to pass between an environment exterior to the elongate member second portion lumen 1926 and the elongate member second portion lumen 1926. For example, each pore of the plurality of pores 1932 can be used to perform a procedure such as suction and/or irrigation procedures.

While a plurality of pores 1932 have been illustrated, an elongate member can define any suitable number of pores, and skilled artisans will be able to select a suitable number of pores to define on an elongate member of a medical device according to a particular embodiment based on various considerations, including the treatment intended to be performed. Example number of pores considered suitable to define on an elongate member of a medical device include one, at least one, two, a plurality, three, four, five, six, and any other number considered suitable for a particular embodiment.

In the illustrated embodiment, the cap 1914 is releasably attached to the elongate member first portion 1910. The cap 1914 comprises a proximal end 1934, a distal end 1936, and a body 1938 that defines a first opening 1940, a second opening 1942, a lumen 1944, and threads 1946. The first opening 1940 is defined on the proximal end 1934 and the second opening 1942 is defined on the distal end 1936. The lumen 1944 extends from the first opening 1940 to the second opening 1942.

The lumen 1944 has a first inside diameter 1943 and a second inside diameter 1945. The first inside diameter 1943 is disposed along a proximal portion of the lumen 1944 that extends from the proximal end 1934 of the cap 1914 toward the distal end 1936 of the cap 1914. The second inside diameter 1945 is less than the first inside diameter 1943 and is disposed along a distal portion of the lumen 1944 that extends from the distal end 1936 toward the proximal end 1941. The first inside diameter 1943 tapers to the second inside diameter 1945 along a tapered portion 1948 of the inner surface of the cap 1914 defined between the proximal portion and the distal portion of the cap 1914. Thus, the tapered portion 1948 of the cap 1914 is disposed between the proximal end 1934 and the distal end 1936 of the cap 1914. In the illustrated embodiment, the tapered portion 1948 of the lumen 1944 corresponds to the tapered distal end 1732 of the elongate member first portion 1912 and the flared proximal end 1918 of the elongate member second portion 1912. However, alternative embodiments can include a cap that has a first inside diameter that tapers to a second inside diameter along a portion, or the entirety, of the length of the cap (e.g., along a proximal portion of the cap that extends from the proximal end toward the distal end, along a distal portion of the cap that extends from the distal end toward the proximal end).

Threads 1946 are disposed between the proximal end 1934 and the distal end 1936 of the cap 1914 within lumen 1944 and have a helical configuration that is sized and configured to interact with the helical configuration defined by threads 1916 defined by the elongate member first portion 1910. Threads 1946 provide a mechanism to releasably attach the cap 1914 to the elongate member first portion 1910. While the threads 1946 have been illustrated as defined on an inner surface of the cap 1914, the threads defined by a cap can alternatively be defined on the outer surface of the cap. Alternative embodiments can include threads that extend from the proximal end of a cap toward the distal end of the cap.

An example method of assembling the medical device 1710 comprises passing the distal end 1920 of the elongate member second portion 1912 through the lumen 1944 defined by the cap 1914 such that the flared proximal end 1918 contacts the inner wall of the cap 1914. Subsequently, the cap 1914 can be advanced toward the elongate member first portion 1910 such that the cap 1914 contacts the elongate member first portion 1910. Torque is then applied to the cap 1914 and/or the elongate member first portion 1910 (e.g., in a clockwise direction about the lengthwise axis of the elongate member first portion 1910 and/or cap 1914, in a counterclockwise direction about the lengthwise axis of the elongate member first portion 1910 and/or 1914) until a sealed, or substantially sealed, engagement between the elongate member first portion 1910, elongate member second portion 1912, and/or the cap 1914 is accomplished. In the assembled configuration, the lumen 1740 of the elongate member first portion 1910 and the lumen 1926 of the elongate member second portion 1912 are in communication with one another and are coaxial. However, alternative embodiments can include an assembled medical device that includes an elongate member first portion that is not coaxial with an elongate member second portion.

In the embodiment illustrated, the tension member 1720 extends from the first end 1784, along a portion of the outer surface of the elongate member second portion 1912, through the passageway 1752 and into the elongate member lumen 1926 defined by the elongate member second portion 1912, through a portion of the lumen 1926, through a portion of the lumen 1740 defined by the elongate member first portion 1910, through the first plug passageway 1766, through a first portion of the chamber 1742, through the cutting element passageway 1846, through a second portion of the chamber 1742, and through the second plug passageway 1780. The tension member 1720 is movable between a first position and a second position such that when the tension member 1720 is in the first position the elongate member 1714 is in the first configuration, as shown in FIG. 17, and when the tension member 1720 is in the second position the elongate member 1714 is in the second configuration, as shown in FIG. 18.

In the illustrated embodiment, when the elongate member 1714 is in the first configuration, the passageway 1752 defined by the elongate member second portion 1912 is disposed on a first plane that contains the lengthwise axis of the elongate member second portion 1912 and the attachment location of the first end 1784 of the tension member 1720 is disposed on a second plane that contains the lengthwise axis of the elongate member second portion 1912. In the illustrated embodiment, the first plane is disposed at a 180 degree angle to the second plane (e.g., the first plane is coplanar with the second plane) such that the passageway 1752 is disposed on a first side of the wall 1924 and the attachment location is disposed on an opposably facing second side of the wall 1924. However, alternative embodiments can define any suitable angle between a first plane and a second plane depending on the desired curvature intended to be imparted on an elongate member, such as angles that are equal to, substantially equal to, or about, 180 degrees, 90, degrees, 45 degrees, and any other angle considered suitable for a particular embodiment.

While an interlocking structure has been illustrated between the elongate member first portion 1910 and the cap 1914 to secure the elongate member second portion 1912 to the elongate member first portion 1910, any suitable locking structure can be included on an elongate member first portion, elongate member second portion, and/or a cap to provide releasable attachment between the elongate member first portion and the elongate member second portion. For example, a cap can be omitted and an elongate member first portion can be directly attached to the elongate member second portion. Skilled artisans will be able to select a suitable locking structure to include on an elongate member first portion, elongate member second portion, and/or cap according to a particular embodiment based on various considerations, including the material(s) that forms the elongate member first portion, elongate member second portion, and/or the cap. Example locking structures considered suitable to include on an elongate member first portion, elongate member second portion, and/or a cap include interlocking structures, structures that provide a friction fit between the elongate member first portion, elongate member second portion, and/or the cap, morse taper configurations, threaded connections, structures that provide a snap fit between the elongate member first portion, elongate member second portion, and/or the cap, mechanical fasteners, and any other structure considered suitable for a particular embodiment. Alternatively, an elongate member first portion can be attached to an elongate member second portion and/or a cap by fusing one or more of the elements to each other, or using any other technique or method of attachment, such as adhesives.

Those with ordinary skill in the art will appreciate that various modifications and alternatives for the described and illustrated embodiments can be developed in light of the overall teachings of the disclosure. Accordingly, the particular arrangements disclosed are intended to be illustrative only and not limiting as to the scope of the invention, which is to be given the full breadth of the appended claims and any and all equivalents thereof.

What is claimed is:

1. A medical device comprising:
an elongate member having a proximal end, a distal end, and an elongate member body defining an elongate member lumen, a first chamber, a first passageway, and a second passageway, the first passageway providing access between an environment exterior to the first chamber and the first chamber, the second passageway providing access between the first chamber and an environment exterior to the first chamber, the elongate member moveable between a first configuration and a second configuration that defines a curve;
a first plug disposed within the first passageway and having a first plug body defining a first plug passageway;
a second plug disposed within the second passageway and having a second plug body defining a second plug passageway;
a tension member having a first end and a second end, the first end attached to the elongate member, the tension member extending from the first end, through the first plug passageway, through the first chamber, and through the second plug passageway, the tension member moveable between a first position and a second position such that when the tension member is in the first position the elongate member is in the first configuration and when the tension member is in the second position the elongate member is in the second configuration; and
a first material disposed within the first chamber and configured to seal the first chamber such that fluid is prevented from moving through the first chamber as the tension member is moved between its first position and second position;
further comprising:
a flexible member attached to the elongate member and having a flexible member body, the flexible member body and the elongate member body cooperatively defining the first chamber, the flexible member moveable between a first position and a second position;
a cutting element attached to the flexible member and disposed within the first chamber;
a membrane disposed within the first chamber and defining a second chamber within the first chamber, the membrane separating the second chamber from the first chamber when the flexible member is in the first position and the cutting element damaging the membrane when the flexible member is in the second position such that the second chamber is in fluid communication with the first chamber;
a second material disposed within the second chamber, the second material separated from the first material when the flexible member is in the first position, the second material in fluid communication with the first material when the flexible member is in the second position.

2. The medical device of claim 1, wherein only the membrane defines the second chamber.

3. The medical device of claim 1, wherein the elongate member body and the membrane cooperatively define the second chamber.

4. The medical device of claim 1, wherein the first material disposed within the first chamber comprises a first part of a liquid hardenable solution; and
wherein the second material disposed within the second chamber comprises a second part of a liquid hardenable solution.

5. The medical device of claim 4, wherein the first part of the liquid hardenable solution comprises an epoxy hardener; and wherein the second part of the liquid hardenable solution comprises an epoxy resin.

6. The medical device of claim 1, wherein the cutting element has a cutting element body that defines a cutting element passageway through the cutting element; and wherein the tension member extends through the cutting element passageway.

7. A medical device comprising:

an elongate member having a proximal end, a distal end, and an elongate member body defining an elongate member lumen, a first chamber wall, a first passageway, and a second passageway, the first chamber wall defining a first chamber, the first passageway providing access between an environment exterior to the first chamber and the first chamber, the second passageway providing access between the first chamber and an environment exterior to the first chamber, the elongate member moveable between a first configuration and a second configuration that defines a curve;

a first plug disposed within the first passageway and having a first plug body defining a first plug passageway, a portion of the first plug extending into the elongate member lumen;

a second plug disposed within the second passageway and having a second plug body defining a second plug passageway;

a flexible member attached to the elongate member and having a flexible member body defining a second chamber wall that cooperatively defines the first chamber with the first chamber wall, the flexible member moveable between a first position and a second position;

a tension member having a first end and a second end, the first end attached to the elongate member, the tension member extending from the first end, through the first plug passageway, through the first chamber, and through the second plug passageway, the tension member moveable between a first position and a second position such that when the tension member is in the first position the elongate member is in the first configuration and when the tension member is in the second position the elongate member is in the second configuration;

a cutting element attached to the flexible member and disposed within the first chamber;

a membrane disposed within the first chamber and defining a second chamber within the first chamber, the membrane separating the second chamber from the first chamber when the flexible member is in the first position and the cutting element damaging the membrane when the flexible member is in the second position such that the second chamber is in fluid communication with the first chamber;

a first material disposed within the first chamber and configured to seal the first chamber such that fluid is prevented from moving through the first chamber as the tension member is moved between its first position and second position; and a second material disposed within the second chamber, the second material separated from the first material when the flexible member is in the first position, the second material in fluid communication with the first material when the flexible member is in the second position.

8. The medical device of claim 7, wherein the second plug passageway is in communication with the elongate member lumen.

9. The medical device of claim 7, wherein the first material disposed within the first chamber has a viscosity that is greater than 1000 centipoise.

10. The medical device of claim 7, wherein only the membrane defines the second chamber.

11. The medical device of claim 7, wherein the elongate member body and the membrane cooperatively define the second chamber.

12. The medical device of claim 7, wherein the first material disposed within the first chamber comprises a first part of a liquid hardenable solution; and wherein the second material disposed within the second chamber comprises a second part of a liquid hardenable solution.

13. The medical device of claim 12, wherein the first part of the liquid hardenable solution comprises an epoxy hardener; and wherein the second part of the liquid hardenable solution comprises an epoxy resin.

14. The medical device of claim 7, wherein the cutting element has a cutting element body that defines a cutting element passageway through the cutting element; and wherein the tension member extends through the cutting element passageway.

15. A medical device comprising:

an elongate member having a proximal end, a distal end, and an elongate member body defining an elongate member lumen, a first chamber wall, a first passageway, and a second passageway, the first chamber wall defining a first chamber, the first passageway providing access between an environment exterior to the first chamber and the first chamber, the second passageway providing access between the first chamber and an environment exterior to the first chamber, the elongate member moveable between a first configuration and a second configuration that defines a curve;

a first plug disposed within the first passageway and having a first plug body defining a first plug passageway in communication with the elongate member lumen, a portion of the first plug extending into the elongate member lumen;

a second plug disposed within the second passageway and having a second plug body defining a second plug passageway;

a flexible member attached to the elongate member and having a flexible member body defining a second chamber wall that cooperatively defines the first chamber with the first chamber wall, the flexible member moveable between a first position and a second position;

a tension member having a first end and a second end, the first end attached to the elongate member, the tension member extending from the first end, through the first plug passageway, through the first chamber, and through the second plug passageway, the tension member moveable between a first position and a second position such that when the tension member is in the first position the elongate member is in the first configuration and when the tension member is in the second position the elongate member is in the second configuration;

a cutting element attached to the flexible member and disposed within the first chamber;

a membrane disposed within the first chamber and defining a second chamber within the first chamber, the membrane separating the second chamber from the first chamber when the flexible member is in the first position and the cutting element damaging the membrane when the flexible member is in the second position such that the second chamber is in fluid communication with the first chamber;

a first material disposed within the first chamber and configured to seal the first chamber such that fluid is prevented from moving through the first chamber as the tension member is moved between its first position and second position, the first material comprising a first part of a liquid hardenable solution; and a second material disposed within the second chamber, the second material separated from the first material when the flexible member is in the first position, the second material in fluid communication with the first material when the flexible member is in the second position, the second material comprising a second part of a liquid hardenable solution.

* * * * *